United States Patent
Prusiner et al.

(10) Patent No.: US 7,166,477 B2
(45) Date of Patent: *Jan. 23, 2007

(54) MUSCLE SAMPLE PREPARED FOR PRION ASSAY

(75) Inventors: Stanley B. Prusiner, San Francisco, CA (US); Patrick Bosque, Denver, CO (US)

(73) Assignee: The Regents of the University of California, Oakland, CA (US)

( * ) Notice: Subject to any disclaimer, the term of this patent is extended or adjusted under 35 U.S.C. 154(b) by 645 days.

This patent is subject to a terminal disclaimer.

(21) Appl. No.: 10/211,942

(22) Filed: Aug. 2, 2002

(65) Prior Publication Data

US 2003/0134337 A1 Jul. 17, 2003

Related U.S. Application Data

(60) Provisional application No. 60/351,525, filed on Jan. 22, 2002, provisional application No. 60/323,903, filed on Sep. 20, 2001.

(51) Int. Cl.
*G01N 33/539* (2006.01)
*G01N 33/00* (2006.01)

(52) U.S. Cl. .......................... 436/539; 435/1.1; 435/7.1; 435/7.21; 435/23; 435/287.2; 435/380; 435/962; 530/412; 530/419; 436/517; 436/524; 436/528; 436/534; 436/536; 436/538; 436/17; 436/166; 436/174; 436/175; 436/177

(58) Field of Classification Search ................ 435/7.1, 435/7.21, 6, 23, 1.1, 287.2, 380; 530/402, 530/403, 412, 419; 436/518, 524, 528, 534, 436/63, 536, 147, 538, 148, 539, 166, 547, 436/174–177, 811, 825, 517, 17
See application file for complete search history.

(56) References Cited

U.S. PATENT DOCUMENTS 5,891,641 A 4/1999 Prusiner et al.

(Continued)

FOREIGN PATENT DOCUMENTS

WO WO 99/42829 8/1999

OTHER PUBLICATIONS

Wadsworth et al., Tissue distribution of protease resistant prion protein in variant Creutzfeldt-Jakob disease using a highly sensitive immunoblotting assay, The Lancet 358: 171-180 (Jul. 21, 2001).*

(Continued)

*Primary Examiner*—Long V. Le
*Assistant Examiner*—Gailene R. Gabel
(74) *Attorney, Agent, or Firm*—Karl Bozicevic; Bozicevic, Field & Francis LLP

(57) ABSTRACT

A method of preparing a sample of muscle tissue and of assaying the prepared sample to determine the presence of prions in the sample is disclosed. The muscle tissue is homogenized and mixed with a complexing agent which forms a complex with a higher specific gravity than $PrP^{Sc}$, the complexing agent or other components of the homogenate. Gravity is then used (e.g. ultra centrifugation) to concentrate the complex and the concentrate is assayed to detect prions. The muscle tissue is preferably extracted from a muscle or group of muscles such as hind limb muscle which have a higher or more preferably the highest concentration of prions as compared to other muscle in the mammal.

7 Claims, 9 Drawing Sheets

U.S. PATENT DOCUMENTS

| | | | | |
|---|---|---|---|---|
| 5,977,324 | A | * | 11/1999 | Prusiner et al. ............. 530/418 |
| 6,166,187 | A | * | 12/2000 | Prusiner et al. ............. 530/419 |
| 2003/0208052 | A1 | * | 11/2003 | Prusiner et al. ............. 530/419 |

OTHER PUBLICATIONS

Chiesa et al., Primary Myopathy and Accumulation of PrPSc-like molecules in peripheral tissues of transgenic mice expressing a prion protein insertional mutation, Neurobiology of Disease 8: 279-299 (May 3, 2001).*

Westaway et al., Degeneration of skeletal muscle, peripheral nerves, and the central nervous system in transgenic mice expressing wild-type prion proteins, Cell 76 (1): 117-129 (Jan. 14, 1994).*

Bosque et al., "Prions in Skeletal Muscle" *PNAS* 99(6):3812-2817 (Mar. 19, 2002).

Chiesa et al., "Primary Myopathy and Accumulation of $PrP^{Sc}$-Like Molecules in Peripheral Tissues of Transgenic Mice Expressing a Prion Protein Insertional Mutation." *Neurobiology of Disease* 8:279-288 (2001).

Wadsworth et al., "Tissue distribution of protease resistant prion protein in variant Creutzfeldt-Jakob disease using a highly sensitive immunoblotting assay." *The Lancet* 358:171-170 (Jul. 21, 2001).

Bendheim, et al., "Nearly ubiquitous tissue distribution of the scrapie agent precursor protein," *Neurology*, 42:149-156 (1992).

Bueler, et al., "Mice devoid of PrP are resistant to Scrapie", *Cell*, 73:1339-1347 (1993).

Carp, "Transmission of scrapie by oral route: effect of gingival scarification," *Lancet*, 1:170-171 (1982).

Eklund, et al., "Pathogenesis of scrapie virus infection in the mouse," *J. Infect. Dis.*, 117:15-22 (1967).

Hadlow, et al., "Virologic and neurohistologic finding in diary goats affected with natural scrapie," *Vet. Pathol.*, 17:187-199 (1980).

Horiuchi, et al., "A cellular form of prion protein (PrPC) exists in many non-neuronal tissues of sheep," *J. Gen. Virol.*, 76:2583-2587 (1995).

Prusiner, "Novel proteinaceous infectious particles cause scrapie" *Science*, 216:136-144 (1982).

Prusiner, et al., "Ablation of the prion protein (PrP) gene in mice prevents scrapie and facilitates production of anti-PrP antibodies," *Proc. Natl. Acad. Sci USA*, 90:10608-10612 (1993).

Prusiner, et al., "Immunological and molecular biological studies of prion proteins in bovine spongiform encephalopathy," *J. Infect. Dis.*, 167:602-613 (1993).

Scott, et al., "Compelling transgenetic evidence for transmission of bovine spongiform encephalopathy prions to humans," *Proc. Natl. Acad. Sci. USA*, 96:15137-15142 (1999).

Spraker, et al., "Spongiform encephalopathy in free-ranging mule deer (Odocoileus hemionus), white-tailed deer (Odocoileus virginianus) Rocky Mountainer elk (Cervus elaphus nelsoni) in northcentral Colorado," *J. Wildl. Dis.*, 33:1-6 (1997).

Will, et al., "Deaths from variant Creutzfeldt-Jakob disease," *Lancet*, 353:979 (1999).

Askanas, Valerie et al., "Prion protein is strongly immunolocalized at the postsynaptic domain of human normal neuromuscular junctions" *Neuroscience Letters*, vol. 159, No. 1-2 (1993) pp. 111-114.

Bendheim, P.E. et al., "Nearly Ubiquitous Tissue Distribution of the Scrapie Agent Precursor Protein" *Neurology*, Lippincott Williams & Wilkins, Philadelphia, US, vol. 42, (Jan. 1992), pp. 149-156.

Horiuchi, M. et al., "A Cellular Form of Prion Protein ($PRP^C$) Exists in Many Non-Neuronaltissues of Sheep" *Journal of General Virology*, Society for General Microbiology, Spencers Wood, GB, vol. 76 (1995) pp. 2583-2587.

* cited by examiner

FIG. 6A
FIG. 6B
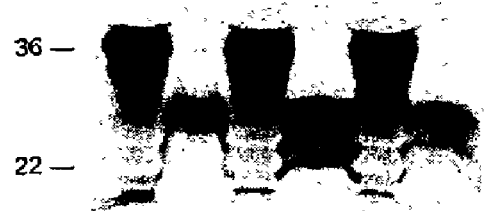
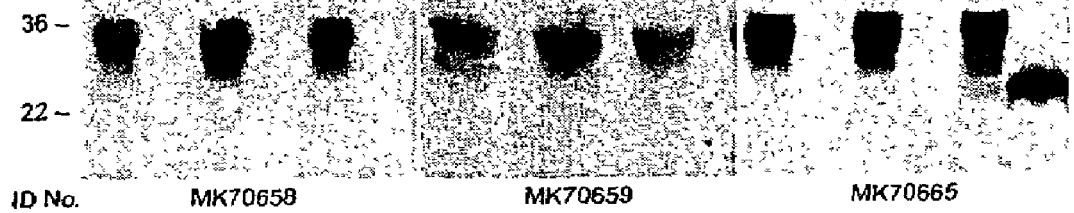
FIG. 6C

MUSCLE SAMPLE PREPARED FOR PRION ASSAY

CROSS-REFERENCES

This application claims the benefit of U.S. Provisional Application No. 60/351,525, filed Jan. 22, 2002 and U.S. Provisional Application No. 60/323,903, filed Sep. 20, 2001, which applications are incorporated herein by reference.

GOVERNMENT RIGHTS

The United States Government may have certain rights in this application pursuant to Grant No. AG 10770 which was awarded by the National Institutes of Health.

FIELD OF THE INVENTION

The present invention relates generally to preparing samples of muscle tissue and assaying same for the presence of prions.

BACKGROUND OF THE INVENTION

Prions cause neurodegenerative diseases, including CJD, BSE, and scrapie in mammals (Prusiner, "Novel proteinaceous infectious particles cause scrapie" *Science*, 216:136–144 (1982)). In animals with clinical signs of scrapie, the highest levels of prions are found in the brain and spinal cord, but other tissues, particularly those of the reticulo endothelial system, exhibit substantial prion titers {Eklund, et al. "Pathogenesis of scrapie virus infection in the mouse," *J. Infect. Dis.*, 117:15–22 (1967); Hadlow, et al., "Virologic and neurohistologic finding in diary goats affected with natural scrapie," *Vet. Pathol.*, 17:187–199 (1980)). Transmission of prions by oral ingestion of infected tissues is well documented in rodents and more recently in cattle and sheep (Prusiner, et al., "Immunological and molecular biological studies of prion proteins in bovine spongiform encephalopathy," *J. Infect. Dis.*, 167:602–613 (1993); Carp, "Transmission of scrapie by oral route: effect of gingival scarification," *Lancet*, 1:170–171 (1982); Phillips et al., *The BSE Inquiry* (Stationery Office, London) (2000)). Although BSE prions have clearly been transmitted to teenagers and young adults from cattle[Will, et al., "Deaths from variant Creutzfeldt-Jakob disease," *Lancet*, 353:979 (1999); Scott, et al., "Compelling transgenetic evidence for transmission of *bovine spongiform* encephalopathy prions to humans," *Proc. Natl. Acad. Sci. USA*, 96:15137–15142 (1999)), it remains unclear whether cervid prions in North America have transmitted to humans [Spraker, et al., "Spongiform encephalopathy in free-ranging mule deer (*Odocoileus hemionus*), white-tailed deer (*Odocoileus virginianus*), and Rocky Mountainer elk (*Cervus elaphus nelsoni*) in northcentral Colorado," *J. Wildl. Dis.*, 33:1–6 (1997)).

The only known constituent of the prion is an abnormal PrP isoform ($PrP^{Sc}$) derived from the normal cell-surface glycoprotein ($PrP^{C}$), the expression of which is necessary for the production of prions (Büeler, et al., "Mice devoid of PrP are resistant to scrapie," *Cell*, 73:1339–1347 (1993); Prusiner, et al., "Ablation of the prion protein (PrP) gene in mice prevents scrapie and facilitates production of anti-PrP antibodies," *Proc. Natl. Acad. Sci USA*, 90:10608–10612 (1993)). Western blot analysis demonstrated that in both mice and cattle (*Bos taurus*), $PrP^{C}$ is expressed in skeletal muscle at a level about 5 to 10% of that in brain (FIG. 1), which is in agreement with earlier reports (Horiuchi, et al., "A cellular form of prion protein ($PrP^{C}$) exists in many non-neuronal tissues of sheep," *J. Gen. Virol.*, 76:2583–2587 (1995); Bendheim, et al., "Nearly ubiquitous tissue distribution of the scrapie agent precursor protein," *Neurology*, 42:149–156 (1992)).

SUMMARY OF THE INVENTION

The invention is based, in part, on unexpectedly finding that prions are found in muscle tissues in sufficiently high concentration to be detected by currently available assays. The ability to detect prions in muscle is enhanced by using sample preparation methodology as described and disclosed here. Muscle tissue is extracted from a mammal such as a cow and homogenized. Prions in the homogenate are concentrated using centrifugation and/or a complexing agent such as sodium phosphotungstate which binds prions and forms a complex with a higher specific gravity then either prions or the complexing agent alone. Using the sample preparation and prion concentration methodology taught here prions are found in muscle tissue at levels which are about 100 to about 1,000 times higher than the concentration of prions found in blood. Prions in muscle are detected here even though they are present in muscle tissue at levels which are about $1/100$ to about $1/1,000$ the levels at which prions are found in brain tissue.

In addition to the unexpected finding that prions are found in muscle it has also been unexpectedly found that prions are present in higher concentrations in some muscles or muscle groups as compared to other muscles or muscle groups. The concentration of prions in different muscle groups can be mapped to find the muscles where the highest concentration of prions is likely to be in any given mammal species. The hind limb muscles are believed to contain the highest concentration of prions based on data provided here.

An aspect of the invention is applying any type of assay method to a sample of muscle tissue to detect the presence of prions and/or $PrP^{Sc}$ therein.

A feature of the invention is that muscle tissue is prepared in a manner whereby $PrP^{Sc}$ in the muscle tissue is concentrated to prepare for assaying.

An advantage of the invention is that muscle tissue can be extracted and assayed without killing the animal from which the muscle is taken.

Another advantage is that assays taught here allow for the detection of both protease-resistant $PrP^{Sc}$ (e.g. PrP27–30) as well as infectivity.

These and other objects, advantages, and features of the invention will become apparent to those persons skilled in the art upon reading the details of the invention as more fully described below.

BRIEF DESCRIPTION OF THE FIGURES

FIG. 6 includes FIGS. 6(a), 6(b) and 6(c) each of which shows lanes showing digestion of $PrP^{Sc}$ in muscle.

DETAILED DESCRIPTION OF THE INVENTION

Figure 1A:
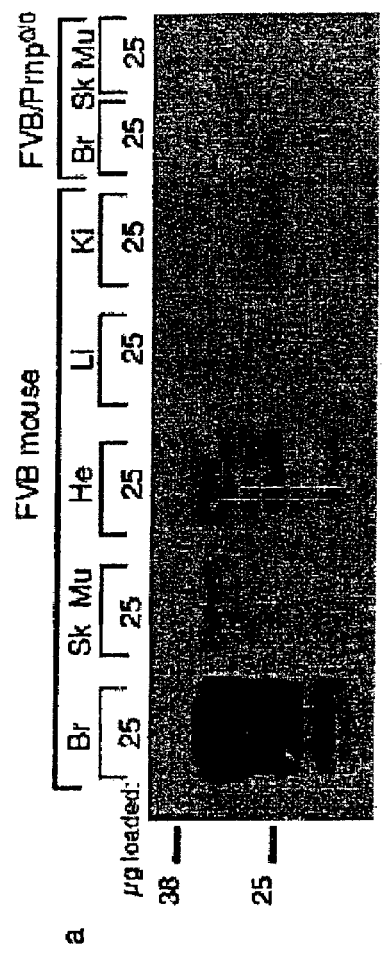
FIG. 1A shows an image of a Western Blot detecting the level of $PrP^{C}$ expression in brain and muscle.

Before the present assays, methods and compositions are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a prion" includes a plurality of such prions and reference to "the antibody" includes reference to one or more antibodies and equivalents thereof known to those skilled in the art, and so forth.

All references and patent applications cited within this application are incorporated by reference in their entirety.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

INVENTION IN GENERAL

Considerable evidence argues that consumption of beef products from cattle infected with bovine spongiform encephalopathy (BSE) prions causes new variant Creutzfeldt-Jakob disease (nvCJD). In an effort to prevent nvCJD, certain "specified offals", including neural and lymphatic tissues, thought to contain high titers of infectious prions have been excluded from foods destined for human consumption (Phillips et al., *The BSE Inquiry* (Stationery Office, London) (2000)).

The present invention shows that mouse skeletal muscle can propagate prions and accumulate measurable titers of these pathogens. Data provided here shows both measurable prion titers and the disease-causing isoform of the prion protein ($PrP^{Sc}$) in the skeletal muscle of wild-type (wt) mice with neurologic signs of experimental scrapie. To determine whether prions are produced or merely accumulate intramuscularly, experiments were carried out to established transgenic mice expressing either mouse or Syrian hamster (SHa) PrP exclusively in muscle. Inoculating these mice intramuscularly (i.m.) with prions resulted in the formation of nascent prions in muscle. In contrast, inoculating mice in which PrP expression was targeted to hepatocytes resulted in very low hepatic prion titers. Thus, the tropism of prions for certain tissues depends on factors other than the amount of PrP expressed and such factors permit the propagation and accumulation of prions in skeletal muscle. Results provided here show that significant dietary exposure to prions is provided through the consumption of meat, even if it is free of neural and lymphatic tissue.

Prior to the present invention it was widely thought that animals which were infected with prions did not have prions or did not have detectable levels of prions within the muscle tissue of the animal. However, using the sample preparation methodology of the present invention it is possible to prepare a muscle sample in such a way so as to concentrate prions present in muscle tissue and find detectable levels of prions within the concentrated sample.

An important aspect of the invention is a method of preparing a sample which comprises obtaining muscle tissue from a mammal which may be any mammal including humans, mice and hamsters, but is more generally a farm animal such as a cow, sheep, horse, chicken, turkey, donkey, etc. The extracted muscle tissue sample is homogenized by any suitable means such as a blender in order to create a flowable homogenate. The homogenate is then subjected to high speed ultracentrifugation. The centrifugation is continued for a period of time sufficient so as to cause prions within the sample to be forced to the bottom of the container in which the centrifugation is carried out. The prions have a higher specific gravity as compared to other proteins due to their somewhat compact configuration as compared to other proteins. The concentrated sample forced to the bottom of the centrifuged container is then subjected to any desired assay for detecting prions. The assay may be a Western Blot, ELISA assay or a conformation-dependent immunoassay (CDI assay) as taught within U.S. Pat. No. 5,891,641 issued Apr. 6, 1999 or an assay as taught within U.S. Pat. No. 6,214,565 issued Apr. 10, 2001 or a direct antibody assay as taught in U.S. Pat. No. 5,846,533, all of which patents are incorporated herein by reference in order to disclose and describe assay methodology for detecting conformationally altered proteins and particularly for detecting prions within the sample.

A preferred aspect of the invention allows for sample preparation wherein the sample is first brought into contact with a complexing agent which binds to PrP$^{Sc}$ or prions within the sample creating a component which has a higher specific gravity as compared with the prions alone. An example of a complexing agent includes heteropoly acids and salts thereof including phosphotungstic acid (PTA) and salts thereof and in particular sodium phosphotungstate (see U.S. Pat. No. 5,977,324 incorporated here to disclose complexing agents and sample preparation methodology in general).

Various other aspects and embodiments of the invention as well as advantages of the invention will become apparent to those of skill in the art upon reading this disclosure. Specific methods of sample preparation and assay methodologies are those encompassed by the claims which form a part of this disclosure.

ASPECTS OF THE INVENTION

The invention includes a method of preparing a sample, comprising the steps of:

obtaining a sample of muscle tissue from a mammal; homogenizing the sample thereby creating a homogenate; contacting the homogenate with a complexing agent which binds $PrP^{Sc}$ in the homogenate forming a complex with a higher specific gravity as compared to the specific gravity of either $PrP^{Sc}$ or the complexing agent alone; and concentrating the complex by the application of gravity.

The muscle tissue is from muscle having a higher concentration of prions than other muscle for the species of mammal from which the sample is obtained. The sample is obtained from muscle having a higher concentration of prions as compared to any other muscle in the mammal from which the muscle is obtained. The sample of muscle tissue is obtained from hind limb muscle of the mammal chosen from a cow, a sheep and a deer wherein the concentration by gravity is enhanced by centriguation. The complexing agent is chosen from a heteropoly acid and a salt thereof, and may be sodium phosphotungstate, and the method may include treating the homogenate under conditions and for a period of time so as to denature $PrP^{C}$ in the homogenate and so as to change the conformation of $PrP^{Sc}$ in the homogenate.

The invention also includes a method for determining the presence of $PrP^{Sc}$ in muscle, comprising the steps of:

contacting homogenized muscle tissue extracted from a muscle tissue with a higher concentration of prions than other muscle tissue for the species of mammal from which the muscle tissue is extracted, the muscle tissue being extracted from a mammal chosen from a human, a cow, a deer and a sheep with a complexing agent which binds $PrP^{Sc}$ forming a complex with a higher specific gravity as compared to the specific gravity of $PrP^{Sc}$;

using force from centrifugation to concentrate the complex in a concentrated sample; analyzing the concentrated sample to determine the presence of $PrP^{Sc}$.

Further the invention includes an assay method, comprising the steps of:

providing a sample of muscle tissue suspected of containing a PrP protein which assumes a first conformation and a second, disease related conformation; concentrating the sample in a manner which concentrates prions present in the sample and thereby provides a concentrated sample; dividing the concentrated sample into a first portion and a second portion; contacting the first portion with a labeled antibody which binds to the PrP protein in its first conformation with a higher degree of affinity than its binds to the PrP protein in its second, disease related conformation; treating the second portion in a manner which causes any PrP protein in the second, disease related conformation to assume a different conformation which conformation has a higher degree of affinity for the labeled antibody as compared to the affinity for the PrP protein in the second disease related conformation; contacting the second portion with the labeled antibody; determining the level of binding of labeled antibody to PrP protein in the first portion; determining the level of binding of labeled antibody to PrP protein in the second portion; and comparing the level of binding of labeled antibody to PrP protein in the first portion with the level in the second portion and thereby determining whether the sample of muscle comprised PrP protein in the disease related second conformation.

In the assay the sample of muscle tissue may be obtained from hind limb muscle of the mammal chosen from a human, cow, sheep and deer; and wherein the concentrating comprise contacting the sample with a complexing agent and subjecting the sample to centrifugation.

The treating maybe carried out by subjecting the second portion to a treatment selected from the group consisting of heat, pressure and chemical exposure in order to convert at least 2% of any PrP protein in the second disease related conformation to the different conformation; wherein the labeled antibody has at least four times greater affinity for the PrP protein in the first conformation than for the PrP protein in the second conformation; or wherein the labeled antibody has at least thirty times greater affinity for the PrP protein in the first conformation than for the PrP protein in the second conformation; or wherein the labeled antibody is Europium-labeled 3F4 IgG; or wherein levels of binding labeled antibody to PrP protein are determined using time-resolved, disassociation-enhanced fluorescence.

Another aspect of the invention includes an assay method, comprising the steps of:

providing a sample of muscle tissue suspected of containing a PrP protein which assumes a first conformation and a second, disease related conformation; concentrating the sample in a manner which concentrates prions present in the sample and thereby provides a concentrated sample; treating the concentrated sample in a manner which causes an PrP protein in the second, disease related conformation to change its conformation to a different conformation having a higher binding affinity to a labeled antibody than the level of binding of said labeled antibody to said second, disease related conformation; contacting the concentrated, treated sample with said labeled antibody which binds to the PrP protein in its first conformation and different conformation with a higher degree of affinity than its binds to the PrP protein in its second, disease related conformation; determining the level of binding of labeled antibody to PrP protein in a sample; comparing the level of labeled binding in the sample to a previously established standard level of binding to a treated standard, which treated standard prior to treatment contains a known amount of PrP protein in (i) the first conformation and (ii) in the second, disease related conformation, and determining the probability of the sample of muscle containing PrP protein in the second, disease related conformation based on the comparison.

In the assay the sample of muscle tissue may be obtained from hind limb muscle of the mammal chosen from a cow, a sheep and a deer, and wherein the level of binding of labeled antibody to PrP protein is determined using flow cytometry.

In the assay the standard may be obtained from previous measurements of the level of PrP protein in equivalent samples of muscle from normal, non-diseased individuals.

In the assay the standard may be obtained from previous measurements of the level of the PrP protein in equivalent samples of muscle from individuals diagnosed with a disease associated with the second, disease related conformation.

Yet another aspect of the invention is an assay method, comprising the steps of:

providing a sample of muscle tissue suspected of containing a PrP protein which assumes a first conformation and a second, disease related conformation; concentrating the sample in a manner which concentrates prions present in the sample and thereby provides a concentrated sample; dividing the concentrated sample in to a first portion and a second portion; contacting the first portion with a labeled antibody which binds to the PrP protein in its first conformation with a higher degree of affinity than it binds to the PrP protein in its second, disease related conformation; treating the second portion in a manner which causes any PrP protein in the second, disease related conformation to assume a different conformation which conformation has a higher degree of affinity for the labeled antibody as compared to the affinity for the PrP protein in the second disease related conformation; contacting the second portion with the labeled antibody; determining the levels of binding of labeled antibody to PrP protein in the first protein; determining the level of binding of labeled antibody to PrP Protein in the second portion; adjusting the determined level of labeled antibody to PrP protein in the second portion to compensate for increasing the affinity of the PrP protein in the first conformation for the antibody resulting from the treating; subtracting the level of binding of labeled antibody protein in the first portion from the adjusted level of binding of labeled antibody in the second portion to obtain a differential; and applying the differential to the formulae below wherein the differential is represented by the)

$$PrP_{S49} \in ) F_{\exists n \bar{\omega} d} = F_d - (F_n * f_{\forall n \bar{\omega} d})$$

wherein each of the above variables is provided below:
F—any detectable signal;
$F_n$—signal of protein in native conformation;
$F_{n\forall}$ and $F_{n\exists}$—signals of native non-disease and disease conformations, respectively;
$F_d$—signal of treated protein;
$F_{d\forall}$ and $F_{d\exists}$—are the signals of treated non-disease and disease conformations;
)$F_{n\bar{\omega}d}$—increase of signal in the transition from native to treated state;
)$F\forall n\bar{\omega}d$—increase in the signal of non-disease conformation in the transition from native to treated state;
)$F\exists n\bar{\omega}d$—increase in the signal of disease conformation in the transition from native to treated state;
$f_{\forall n\bar{\omega}d}$—correlation factor for the transition from native to treated state of non-disease conformation;
$[PrP_\exists]$—concentration of protein in disease conformation;
∈—is proportional to; and
*—is multiply by.

Any method of the invention may include adjusting the determined level of binding of labeled antibody to PrP protein in the second portion to compensate for increasing the affinity of the PrP protein in the first conformation for the antibody resulting from the treating.

Another aspect of the invention is a method, comprising the steps of:

contacting a sample of muscle tissue with a complexing agent which binds to a PrP protein; allowing the complexing agent to remain in contact with the sample of muscle for a period of time and under conditions such that PrP protein in the sample binds to the complexing agent creating a complex with a density greater than the density of either the PrP protein alone or the complexing agent alone; centrifuging the sample at a speed and for a period of time sufficient to separate out complexes of PrP protein bound to the complexing agent to provide a sample concentrate.

The method may further comprise analyzing the PrP protein of the complex to determine characteristics, wherein the characteristics are selected from the group consisting of solubility, three-dimensional structure and infectivity.

The method may further comprise comparing a characteristic of the PrP protein with a same characteristic of a disease conformation of the PrP protein extracted from brain tissue of the same animal from which the muscle was extracted.

In addition, the method of the invention may further comprise:

contacting a first portion of the sample concentrated with a binding partner, said binding partner having a higher affinity for a first conformation than a second pathogenic conformation, and determining a first concentration of binding partner/protein complexes in the first portion; treating a second portion of the sample concentrate to increase binding affinity of the second conformation of the protein to the binding partner; contacting the treated second portion of the sample with the binding partner to determine a second concentration of binding partner/protein complexes in the second treated portion; adjusting the second concentration to provide an adjusted concentration which adjustment compensates for increased affinity of the protein in the first conformation for the binding partner resulting from the treating; and comparing the first concentration with the adjusted concentration to determine the presence of protein in the second pathogenic, conformation.

The method may be carried out, wherein the first concentration and the second concentration are determined using time-resolved dissociation enhanced fluorescence; wherein the second pathogenic conformation of the protein is present in the sample in a concentration of $1 \times 10^3$ particles/ml or less; and wherein the second portion of sample is treated using a treatment selected from the group consisting of heat, pressure, and chemical denaturation, sufficient to convert at least 2% of any protein in the second pathogenic conformation to a conformation with increased binding affinity for the binding partner.

The methods may be one further comprising:

treating the sample concentrate to convert the second conformation of the protein into a binding conformation having an affinity for a binding partner higher than the second conformation; contacting the treated sample with the binding partner to determine a concentration of binding partner/protein complexes in the sample; adjusting the concentration to provide an adjusted concentration which compensates for increased affinity of the first conformation of the protein to the binding partner resulting from the treating; and comparing said adjusted concentration to a known concentration selected from the group consisting of a control concentration and a predetermined standard concentration to determine the presence of the protein in the second conformation in the sample.

Further, the method may be one wherein said binding partner comprises a labeled antibody, the complexing agent comprises a metal salt of phosphotungstic acid, and wherein the concentration is determined using flow cytometry; and wherein the adjusted concentration is compared to a known concentration determined from a treated non-infected control sample; and wherein the adjusted concentration is compared to a known concentration predetermined from a treated sample from a non-infected population of mammals selected from the group consisting of humans, cows and sheep; and wherein the antibody is 3F4 and the complexing agent is sodium phosphotungstate; and wherein the protein in the second conformation is present in the sample in a concentration of $1\times10^3$ protein molecules or less per ml and wherein the protein in the first conformation is present in the sample in a concentration of $1\times10^6$ protein molecules or more per ml.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Homogenates of skeletal muscle and liver were prepared from FVB mice showing signs of scrapie, 128 days after they were inoculated intracerebrally (i.c.) with the Rocky Mountain Laboratory (RML) mouse prion strain. The titers of prions in muscle from these mice, as determined by an incubation time assay, were $10^5$–$10^6$ ID$_{50}$ units/g (see Table 1 below).

These substantial titers of prions in muscle do not represent a general contamination of mouse organs with brain-derived prions because homogenates of liver, an organ that in wt mice expresses almost no $PrP^C$ (Raeber, et al., "Ectopic expression of prion protein (PrP) in T lymphocytes or hepatocytes of PrP knockout mice is insufficient to sustain prion replication," *Proc. Natl. Acad. Sci. USA,* 96:3987–3992 (1999)), from these same mice either failed to transmit scrapie or transmitted to only a few mice, indicating titers of $10^3$ $ID_{50}$ units/g or less. Previous studies demonstrated that brain prion titers in mice exhibiting signs of prion infection are typically $10^9$–$10^{10}$ $ID_{50}$ units/g (Supattapone, et al., "Branched polyamines cure prion-infected neuroblastoma cells," *J. Virol.,* 75:3453–3461 (2001)) when assayed in Tg(MoPrP)4053/FVB mice.

TABLE 1

PRION TITERS IN TISSUES OF WT (FVB) MICE*

| Tissue assayed | Animal no. | Mean incubation time [days ± SEM ($n/n_0$)†] | Log titer $ID_{50}$ units/g‡ ± SEM |
|---|---|---|---|
| Muscle | G70155 | 66 ± 1.7 (10/10) | 6.1 ± 0.2 |
| | G70158 | 70 ± 2.4 (10/10) | 5.6 ± 0.3 |
| | G70155 | 64 ± 2.5 (10/10) | 6.4 ± 0.3 |
| | G70157 | 73 ± 2.1 (10/10) | 5.2 ± 0.3 |
| Liver | G70155 | 103 (2/10) | <3 |
| | G70157 | — (0/10) | <2 |

*Mice were sacrificed when showing signs of neurologic illness, 128 days after intracerebral inoculation with RML prions.
†n, number of animals diagnosed ill with scrapie; $n_0$, number of animals inoculated.
‡Determined by incubation time assay in Tg(MoPrP)4053/FVB mice.

In addition to the infectious prions, protease-resistant $PrP^{Sc}$ was detected in the muscle of inoculated wt mice but not in uninoculated controls and such is shown in FIG. 2. On the Western blot, proteinase K (PK)-digested muscle homogenates of inoculated mice displayed an apparent molecular weight and glycoform ratio identical to that of $PrP^{Sc}$ found in the brain. Comparison of muscle and brain homogenates demonstrated that protease-resistant $PrP^{Sc}$ in muscle was ~500-fold lower than in the brain. This brain/muscle $PrP^{Sc}$ ratio of $10^{2.7}$ is similar to the brain/muscle $ID_{50}$ unit ratio of approximately $10^3$.

FIG. 2 is an image of a Western Blot showing protease-resistant PrP (prions) in muscle tissue of RML-infected CD1 mice. Specifically, lane 1 contains untreated brain homogenate from an uninoculated CD1 mouse. All other lanes contain insoluble pelleted material from proteinase K-digested homogenates of CD1 mouse muscle. No protease-resistant PrP is found in muscle of uninoculated mice (lane 2) whereas $PrP^{Sc}$ is readily detectable in the muscle of mice showing signs of neurologic disease 132 days after intracerebral inoculation with RML prions (lanes 4 and 5). For comparison, brain homogenate from a mouse showing signs of scrapie was diluted 1:1000 into a muscle homogenate from an uninoculated mouse (lane 3). Amounts loaded are expressed as equivalents of total protein (in mg) of starting material, before proteinase digestion and precipitation. Note that lanes 4 and 5 were loaded with the product of twice as much original material as lanes 2 and 3. The blot was probed with the Hum-D13 antibody.

Muscle tissue is composed of a variety of cell types (Engel, et al., *Myology: basic and clinical,* (McGraw-Hill, New York) (1986)), and is intimately associated with neural tissue. To determine whether prions replicate in myofibers themselves, two lines of transgenic (Tg) mice were constructed that express PrP only under the control of myocyte-specific promoters. For each line, transgenes were introduced into FVB mice in which the chromosomal PrP gene had been disrupted ($Prnp^{0/0}$)[Büeler, et al., "Normal development and behaviour of mice lacking the neuronal cell-surface PrP protein," *Nature,* 356:577–582 (1992); Telling, et al., :Interactions between wild-type and mutant prion proteins modulate neurodegeneration in transgenic mice," Genes & Dev., 10:1736–1750 (1996)).

FIGS. 3A, 3B and 3C are all Western Blot images showing the distribution of $PrP^C$ expression in transgenic mice. Specifically, FIG. 3A shows an image of a Western Blot from a Tg(α-actin-MoPrP)6906/$Prnp^{0/0}$ mouse, probed with the polyclonal antibody R073. $PrP^C$ expression in muscle is about 8-fold higher than in wild-type mouse brain (not shown). FIG. 3B shows a Western Blot image from a

Figure 3A:
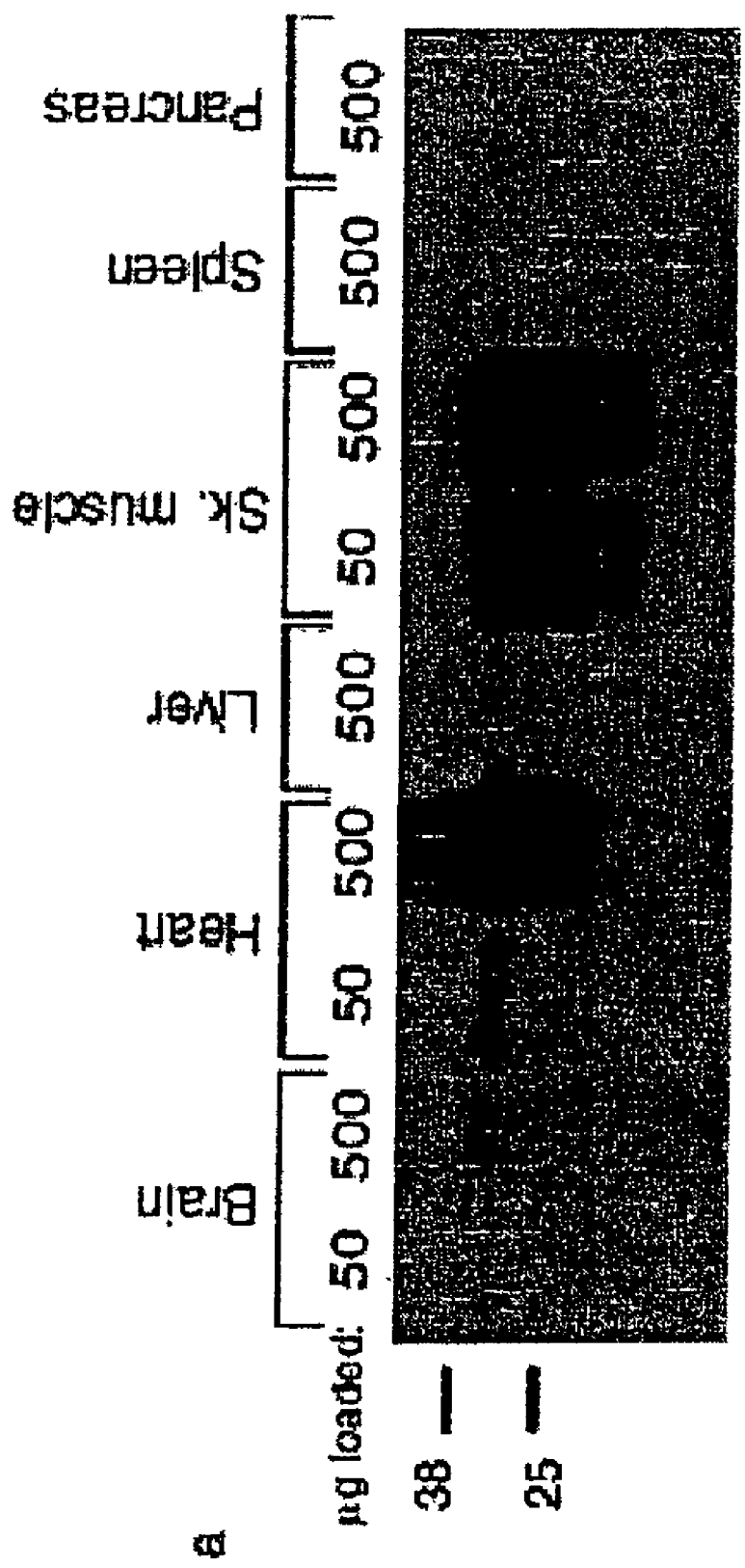
FIGS. 3A, 3B and 3C show images of Western Blots conducted on several different types of tissue extracted from different transgenic mice.
Figure 3B:
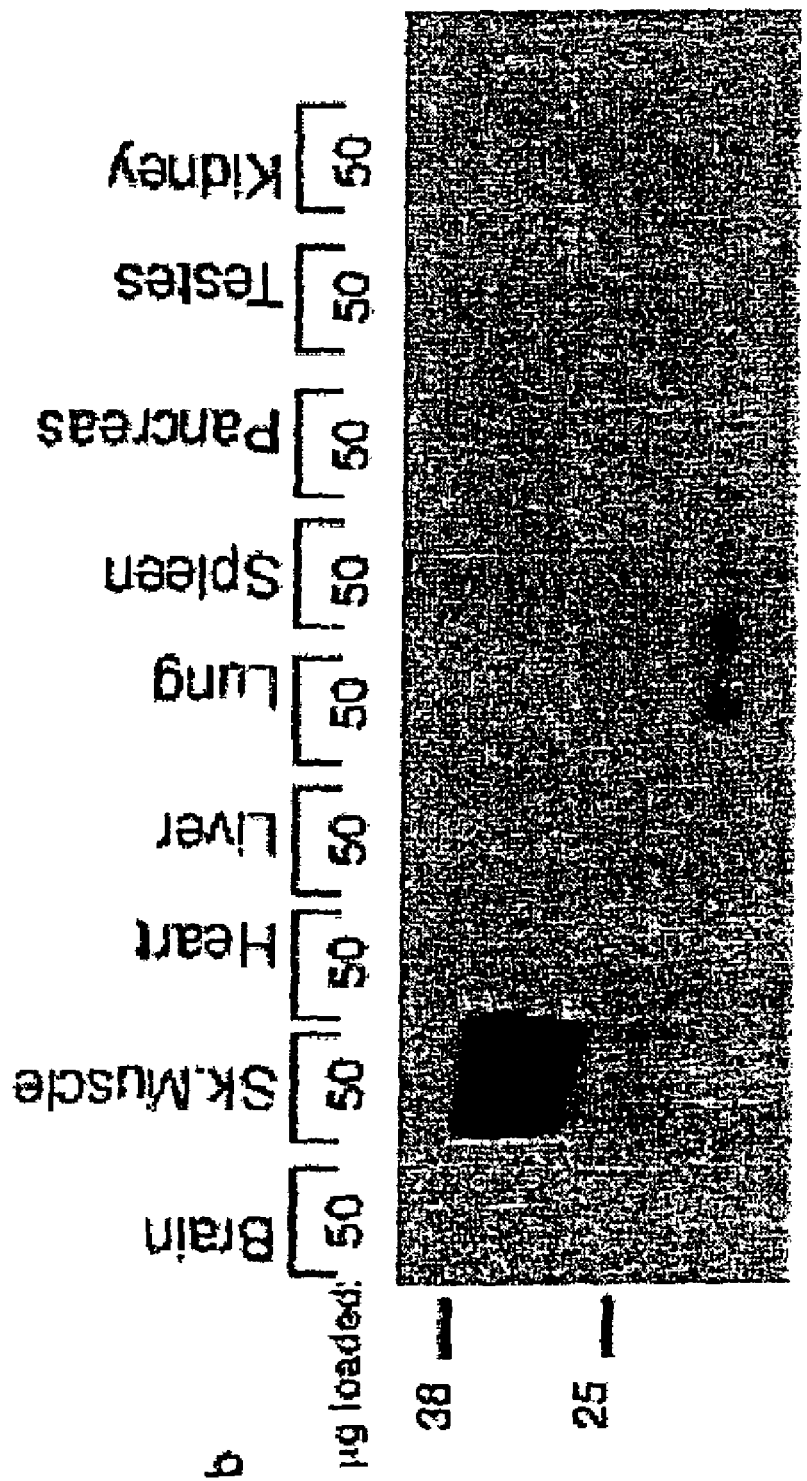
Figure 3C:
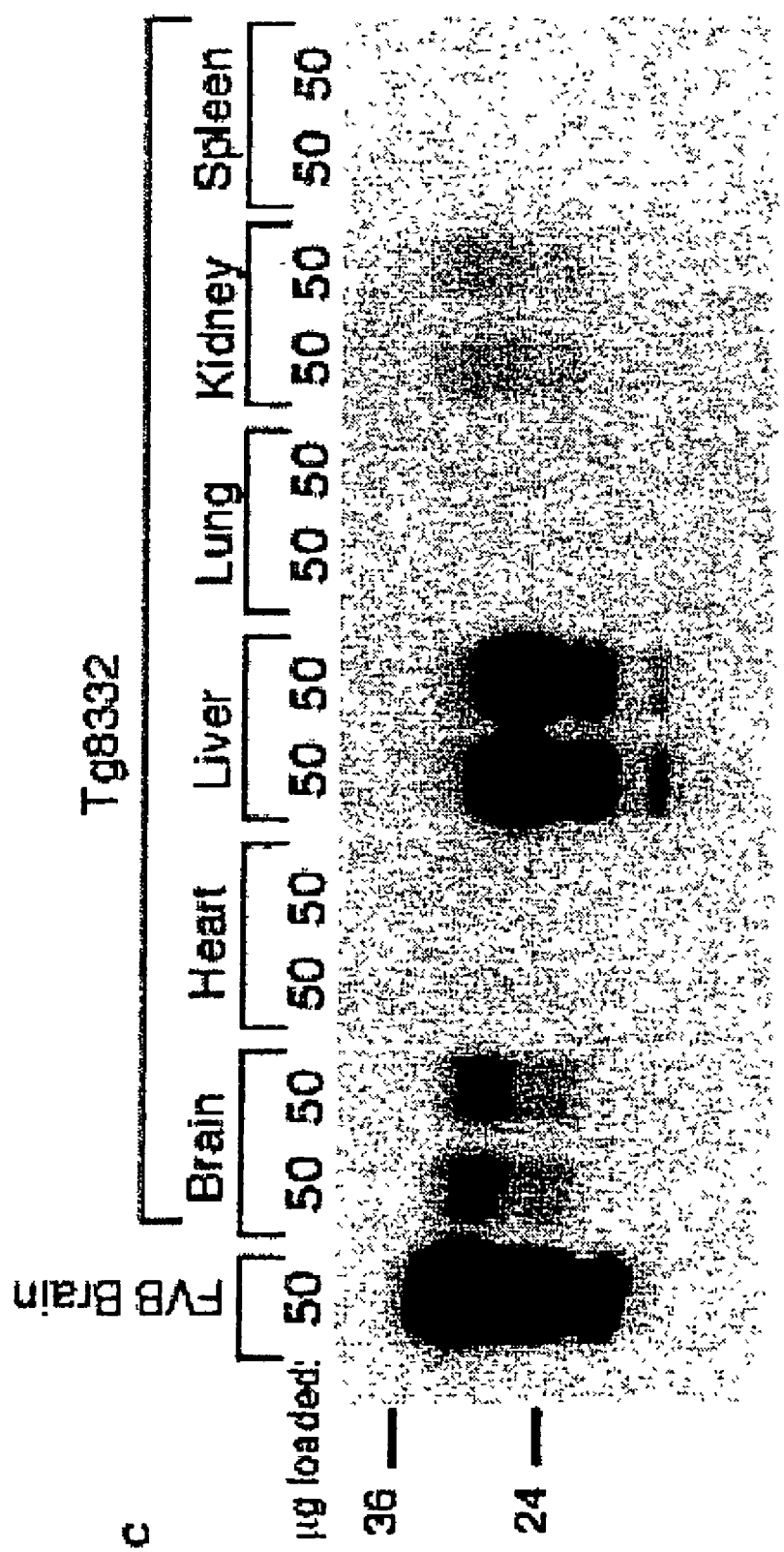

Tg(MCK-SHaPrP)8775/Prnp$^{0/0}$ mouse, probed with 3F4, a monoclonal antibody which recognizes hamster PrP$^C$. PrP$^C$ expression is only detectable in skeletal muscle (Sk. Muscle). A longer exposure of this blot (not shown) reveals trace expression in cardiac muscle, but no PrP$^C$ is detected in any other organ. The low molecular weight bands, seen most prominently in lane 5 (Lung), are also seen when the anti-mouse Ig secondary antibody is used without prior incubation in 3F4. In FIG. 3C homogenates of organs from two Tg(TTR-MoPrP) FVB/Prnp$^{0/0}$ mice are compared to FVB brain. Blot was probed with R073. PrP$^C$ expression in liver is lower than in FVB brain, but higher than in the brain of mice of this transgenic line. A very small amount of PrP is expressed in the kidney. Glycosylated forms of PrP from the liver migrate slightly faster than the corresponding glycoforms from the brain of these same mice or of FVB mice.

In the first line, designated Tg(α-actin-MoPrP)6906/Prnp$^{0/0}$, the chicken a-actin promoter directs expression of the mouse Prnp$^a$ allele. Skeletal muscle from these transgenic mice (FIG. 3a) expresses PrP at a level that is about 8-fold higher than the level found in the brains of wt mice. Low levels of PrP are produced in cardiac muscle and PrP is barely detectable in brain as shown in FIG. 3.

In the second line, designated Tg(MCK-SHaPrP)8775/Prnp$^{0/0}$, the muscle creatine kinase (MCK) promoter drives the expression of SHaPrP. In this line, the level of PrP expression in muscle is 4-fold higher than the level of PrP that is expressed in hamster brain. Tg(MCK-SHaPrP)8775/Prnp$^{0/0}$ mice express low levels of PrP$^C$ in cardiac muscle, and no PrP was detected in the brain as shown in FIG. 3B.

The Tg mice and non-Tg littermates were innoculated intramuscularly (i.m.) in the left hind limb with prions. The mice were then sacrificed at various times after inoculation. Tg(α-actin-MoPrP)6906/Prnp$^{0/0}$ mice were inoculated with mouse RML prions while Tg(MCK-SHaPrP)8775/Prnp$^{0/0}$ mice were inoculated with hamster Sc237 prions. Prion titers in homogenates of muscle from the un-inoculated, contralateral hind limb, brain and spleen were measured by bioassay. The results showed titers of>10$^7$ ID$_{50}$ units/g in Tg(α-actin-MoPrP)6906/Prnp$^{0/0}$ muscle, obtained at 350 days after inoculation. Titers were generally lower in muscles of Tg(MCK-SHaPrP)8775/Prnp$^{0/0}$ mice, measuring ~10$^4$ ID$_{50}$ units/g in two mice and ~10$^8$ ID$_{50}$ units/g in another mouse, all three of which were sacrificed 413 days after inoculation (Table 2). The muscle prion titer in a fourth mouse sacrificed 76 days after inoculation was ~10$^4$ ID$_{50}$ units/g. The results of the assays did not detect prions in muscle homogenates from uninoculated Tg(α-actin-MoPrP) 6906/Prnp$^{0/0}$ and Tg(MCK-SHaPrP)8775/Prnp$^{0/0}$ mice.

Several experiments were performed to confirm that the prions found in muscle were formed therein. Results from two experiments excluded residual inoculum as the source of the prions that we measured. First, FVB/Prnp$^{0/0}$ mice were innoculated, which are incapable of propagating prions (Büeler, et al., "Mice devoid of PrP are resistant to scrapie," *Cell*, 73:1339–1347 (1993); Prusiner, et al., "Ablation of the prion protein (PrP) gene in mice prevents scrapie and facilitates production of anti-PrP antibodies," *Proc. Natl. Acad. Sci USA*, 90:10608–10612 (1993)), with RML prions i.m. in parallel to the experiment using Tg(α-actin-MoPrP) 6906/Prnp$^{0/0}$ mice described above. No prions were detected in the muscle of the FVB/Prnp$^{0/0}$ mice at 350 days post-inoculation, indicating that the prions had been cleared.

Second, because it is conceivable that FVB/Prnp$^{0/0}$ mice clear prions more efficiently than mice expressing PrP$^C$ (Race, et al., "Scrapie infectivity found in resistant species," *Nature*, 392:770 (1998)), both Tg(MCK-SHaPrP)8775/Prnp$^{0/0}$ and FVB/Prnp$^{0/0}$ mice were inoculated with Sc237 prions. Prion titers were then determined in the inoculated muscle at various intervals as shown in Table 3 below. Prions disappeared equally rapidly from both lines. Moreover, the levels of prions found ipsilateral to the injection site at 28 days after inoculation in Tg(MCK-SHaPrP)8775/Prnp$^{0/0}$ mice were at least 10-fold lower than the levels found in mice sacrificed at later times, indicating de novo prion synthesis (compare Tables 2 and 3).

TABLE 2

PRION TITERS IN TISSUES OF TRANSGENIC MICE

| Line | Inoculum (route) | Interval* | Tissue assayed | Animal no. | Mean incubation time [days ± SEM (n/n$_0$)$^\dagger$] | Log titer ID$_{50}$ units/g‡ ± SEM |
|---|---|---|---|---|---|---|
| Tg(MCK-SHaPrP)8775/Prnp$^{0/0}$ | Sc237(i.m) | 413 | muscle | E4041 | 82 ± 1.3 (8/8) | 7.4 ± 0.1 |
| | | 413 | | E4516 | 112 ± 0.7 (8/8) | 4.2 ± 0.1 |
| | | 413 | | E4509 | 114 ± 6.2 (8/8) | 4.0 ± 0.4 |
| | | 76 | | E4515 | 113 ± 2.4 (8.8) | 4.2 ± 0.1 |
| | | 413 | brain | E4509 | — (0/8) | <2 |
| | | 76 | spleen | E4515 | 211 (5/8) | <3 |
| | | 413 | | E4516 | 220 (3/8) | <3 |
| | None | N.A. | muscle | D16745 | — (0/8) | <2 |
| | | | | D16746 | — (0/8) | <2 |
| Tg(α-actin-MoPrP)6906/Prnp$^{0/0}$ | RML(i.m.) | 350 | muscle | E9812 | 58 ± 2 (10/10) | 7.4 ± 0.4 |
| | | 350 | | E9813 | 59 ± 2 (10/10) | 7.2 ± 0.4 |
| | | 350 | brain | E9812 | 105 (2/10) | <3 |
| | | 350 | | E9813 | 126 (4/10) | <3 |
| | | 350 | spleen | E9812 | 424 (3/5) | <3 |
| | | 350 | | E9813 | 201 (6/7) | <3 |
| FVB/Prnp$^{0/0}$ | RML (i.m.) | 350 | muscle | E8979 | — (0/10) | <2 |
| | | 350 | | E8980 | — (0/10) | <2 |

TABLE 2-continued

PRION TITERS IN TISSUES OF TRANSGENIC MICE

| Line | Inoculum (route) | Interval* | Tissue assayed | Animal no. | Mean incubation time [days ± SEM $(n/n_0)$†] | Log titer $ID_{50}$ units/g‡ ± SEM |
|---|---|---|---|---|---|---|
| Tg(TTR-MoPrP)8332/Prnp$^{0/0}$ | RML (i.p.) | 523 | liver | E10176 | 197 (3/10) | <3 |
| | | 523 | | E10177 | 93 ± 3.2 (10/10) | 3.4 ± 0.2 |
| | RML (i.c.) | 296 | liver | MF4691 | 91 ± 2.9 (10/10) | 3.8 ± 0.2 |
| | | 296 | | MF4692 | 97 (7/8) | <3 |
| | | 296 | brain | MF4691 | 51 ± 2.5 (10/10) | 8.8 ± 0.6 |
| | | 296 | | MF4692 | 55 ± 2.1 (10/10) | 8.0 ± 0.5 |
| | None | N.A. | liver | ME9012 | — (0/10) | <2 |

*Number of days from inoculation to sacrifice of animal.
†n, number of animals diagnosed ill with scrapie; $n_0$, number of animals inoculated.
‡Tg(MCK-SHaPrP)8775/Prnp$^{0/0}$ tissue prion titers determined by incubation time assay in Syrian hamsters. All others assayed in Tg(MoPrP)4053/FVB mice.

TABLE 3

DECLINE OF PRION TITERS IN MOUSE MUSCLE AFTER INOCULATION WITH SYRIAN HAMSTER Sc237 PRIONS.

| Line | Interval between inoculation and harvest | Mean incubation time [days ± SEM $(n/n_0)$†] | Log titer* ($ID_{50}$ units/g ± SEM) |
|---|---|---|---|
| Tg(MCK-SHaPrP)8775/PrnP$^{0/0}$ | 4 hours | 112.5 ± 3.3 (8/8) | 3.9 ± 0.3 |
| | | 90 ± 4.3 (8/8) | 6.8 ± 0.5 |
| | 1 day | 85.8 ± 2.0 (8/8) | 6.2 ± 0.2 |
| | | 92.5 ± 1.3 (8/8) | 5.3 ± 0.2 |
| | 7 days | 118 ± 2.3 (8/8) | 3.0 ± 0.1 |
| | | 114.4 ± 4.9 (8/8) | 4.8 ± 0.4 |
| | 28 days | 184.5 ± 4.6 (8/8) | −0.6 ± 0.3 |
| | | — (0/8) | — |
| FVB/Prnp$^{0/0}$ | 4 hours | 87.4 ± 1.0 (8/8) | 6.0 ± 0.1 |
| | | 115.8 ± 1.3 (8/8) | 3.0 ± 0.1 |
| | 1 day | 109.6 ± 2.7 (8/8) | 3.5 ± 0.2 |
| | | 101.9 ± 1.5 (8/8) | 4.2 ± 0.2 |
| | 7 days | 114 ± 3.0 (8/8)) | 3.2 ± 0.2 |
| | | 182.1 ± 8.1 (8/8) | 0.5 ± 0.5 |
| | 28 days | 174.3 ± 5.7 (8/8) | 0.4 ± 0.4 |
| | | 200.3 ± 9.7 (4/8) | — |

†n, number of animals diagnosed ill with scrapie; $n_0$, number of animals inoculated.
*Determined by incubation time assay in i.c.-inoculated hamsters. In some cases, very long incubation periods result in low calculated titers, which are likely to be underestimations (see Methods). These values are reported for purposes of comparison.

In order to exclude the possibility that the prions found in the muscle were contaminants produced elsewhere in our mice, prion titers were determined in the brains and spleens of the Tg mice inoculated i.m. No prions were detected in Tg(MCK-SHaPrP)8775/Prnp$^{0/0}$ mouse brain, but low titers were found in Tg(α-actin-MoPrP)6906/Prnp$^{0/0}$ brain, a finding consistent with the low level of PrP$^C$ produced there. Low prion titers were also found in the spleens of inoculated mice from both lines, which might represent an accumulation of prions formed elsewhere, since Western blot analysis failed to detect splenic PrP in these lines. The titers in spleen and brain were, in all cases, lower than in muscle; therefore, the titers in muscle were unlikely to be due to contamination from other tissues.

Tg(α-actin-MoPrP)6906/Prnp$^{0/0}$ and Tg(MCK-SHaPrP) 8775/Prnp$^{0/0}$ mice spontaneously developed a myopathy, in accord with findings in mice in which PrP$^C$ is overexpressed under control of the SHa PrP promoter (Westaway, et al., "Degeneration of skeletal muscle, peripheral nerves, and the central nervous system in transgenic mice overexpressing wild-type prion proteins," *Cell*, 76:117–129 (1994)). Similar histologic abnormalities were detected in the muscle of prion-inoculated mice and uninoculated, Tg controls.

Having demonstrated that skeletal muscle is intrinsically capable of propagating and accumulating prions, an examination was made on whether this is a property of all PrP-expressing tissue, or whether other factors, which may be found only in some cell types, are needed. A recent study (Raeber, et al., "Ectopic expression of prion protein (PrP) in T lymphocytes or hepatocytes of PrP knockout mice is insufficient to sustain prion replication," *Proc. Natl. Acad. Sci. USA*, 96:3987–3992 (1999)) concluded that prions failed to propagate in hepatocytes or T-cells of Tg mice that express PrP in these cell types. However, Raeber et al. stated that the levels of PrP expression achieved in the livers of their mice were quite low and that the absence of detectable prions in circulating T-cells might have been due to loss of prion-infected cells during natural turnover or because of prion-related toxicity.

To determine whether prions can propagate in hepatocytes, Tg(TTR-MoPrP)8332/Prnp$^{0/0}$ mice were used in a process wherein a fragment of the TTR promoter directs mouse Prnp$^a$ expression simultaneously to the liver and to a subset of brain neurons (See FIG. 3C), with higher PrP levels in liver than in brain. Mice were inoculated i.e. with RML prions and sacrificed when they developed signs of disease, at 296 days. Brain prion titers were $10^8$–$10^9$ ID$_{50}$ units/g whereas hepatic prion titers were only $10^3$–$10^4$ ID$_{50}$ units/g. Mice of the same line were inoculated intraperitoneally (i.p.) with RML prions to test the influence of inoculation site. These mice never appeared ill and were sacrificed 523 days after inoculation. Hepatic prion titers in the mice inoculated i.p. were similar to those of mice inoculated i.c. Although hepatic prion titers were low, it does appear that expressing high levels of PrP$^C$ in liver enhances prion formation, since liver homogenates from Tg(TTR-MoPrP)8332/Prnp$^{0/0}$ mice inoculated with RML prions transmitted scrapie to significantly more mice than did liver homogenates from RML-inoculated FVB mice (Tables 1 and 2, P<0.001, Fisher exact test).

From these data, it was concluded that different cell types accumulate prions with markedly different efficiencies, even when PrP$^C$ expression levels are similar. Comparing three tissues in Tg mice expressing murine PrP$^C$, RML prion titers were ~$10^9$ ID$_{50}$ units/g in brain, ~$10^3$ ID$_{50}$ units/g in liver (for Tg(TTR-MoPrP)8332/Prnp$^{0/0}$ mice)) and $10^7$ ID50 units/g in skeletal muscle (for Tg($\alpha$-actin-MoPrP)6906/Prnp$^{0/0}$ mice). The reason for the differing levels of prion accumulation is not obvious. The apparently different glycosylation of hepatic PrP may contribute to the inefficient prion accumulation seen there, but brain and muscle PrP displayed different levels of accumulation despite indistinguishable glycoforms.

The results provided here demonstrate that muscle is intrinsically capable of propagating prions. Therefore, substantial, measurable prion titers may be found in skeletal muscle even if CNS and lymphatic tissues are carefully excluded from meat. That prion titers in the muscle of scrapie-infected, wt mice are as high as $10^6$ ID50 units/g raise the concern that humans consuming meat from prion-infected animals are at risk for acquiring infection. However, several caveats must be considered when assessing risk of humans developing disease from prion-tainted meat. First, the efficiency of prion accumulation in muscle may vary with either the host species or the prion strain involved. Indeed, in results shown here, mouse RML prions appear to have accumulated more efficiently in muscle than did hamster Sc237 prions. Second, oral transmission is inefficient compared to the i.c. inoculations used for the bioassays used to provide results here. In hamsters, oral exposure is $10^5$- to $10^9$-fold less efficient that the i.c. route (Prusiner, et al., "Transmission of scrapie in hamsters," *J. Infect. Dis.*, 152: 971–978 (1985); Diringer, et al, "Effect of repeated oral infection of hamsters with scrapie," *J. Gen. Virol.*, 79:609–612 (1998)). Finally, the species barrier must be considered. Generally, efficient transmission of prions from one species to another requires a high degree of homology in the amino-acid sequence of PrP between the two species. But, the degree to which amino-acid sequence influences the efficiency of transmission depends upon the strain of the prion involved. In the case of nvCJD prions, Tg mice expressing bovine PrP are much more susceptible to nvCJD prions than are Tg mice expressing either human or chimeric human-mouse PrP (Hill, et al., "The same prion strain causes vCJD and BSE," *Nature*, 389:448–450 (1997); Scott, et al., "Identification of a prion protein epitope modulating transmission of bovine spongiform encephalopathy prions to transgenic mice,"*Proc. Natl. Acad. Sci. USA*, 94:14279–14284 (1999)).

The results provided here indicate prions accumulate in skeletal muscle of cattle with BSE, as well as in deer and elk with chronic wasting disease. Specifically, these results have shown the existence of PrP$^C$ in bovine muscle (FIG. 1), even though we did not test muscle tissue from cattle dying of BSE.

Figure 1B:
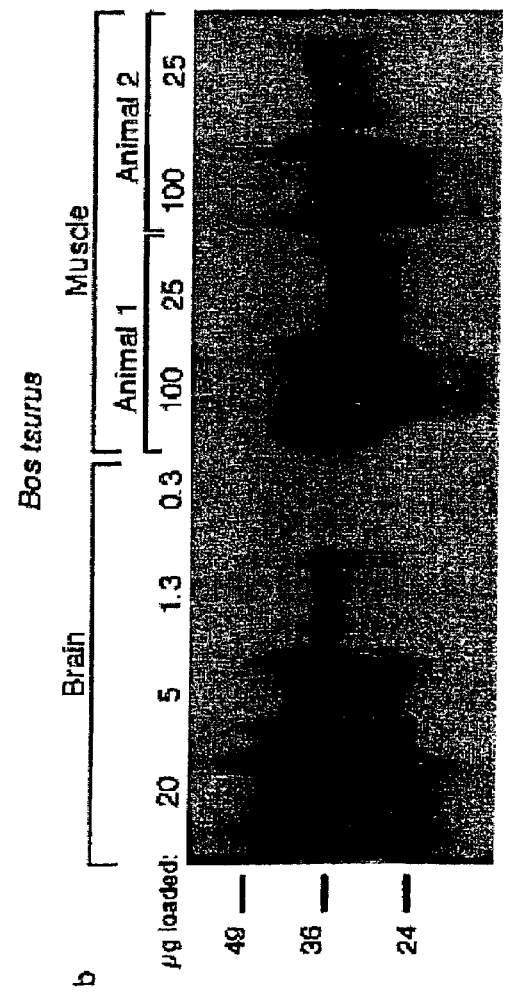
FIG. 1B shows images of Western Blot comparisons of $PrP^{C}$ expression in brain compared to muscle with serial dilutions.
Figure 2:
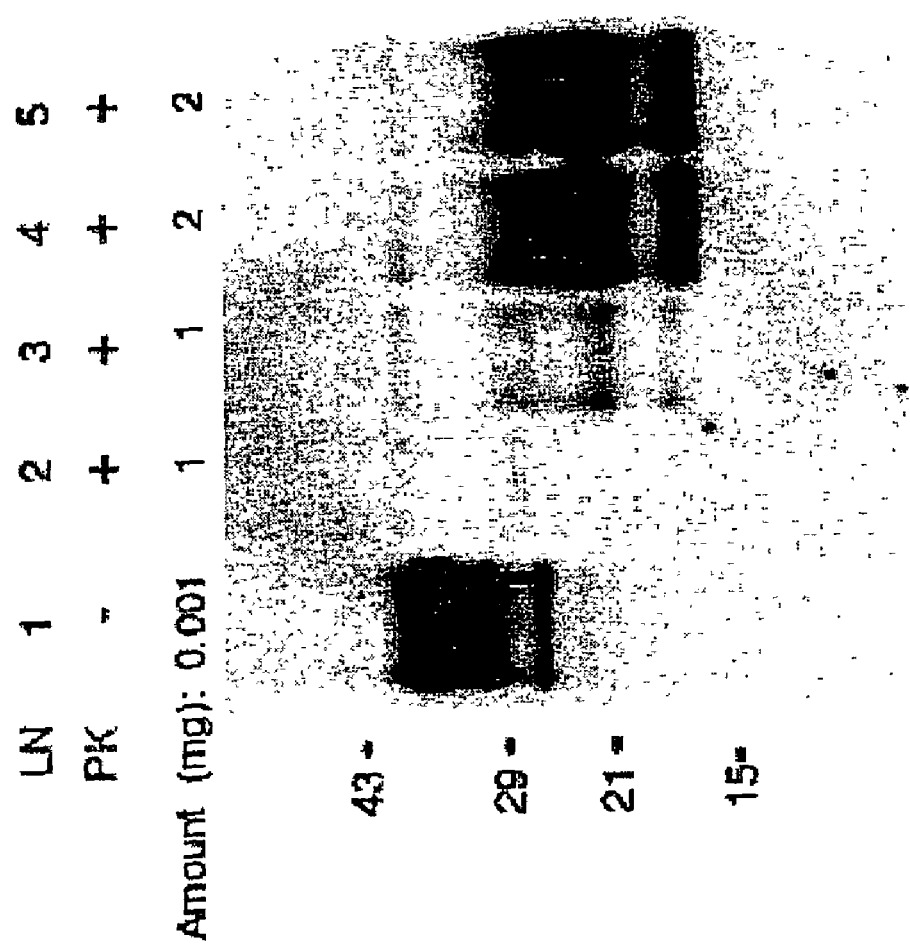
FIG. 2 shows images of five lanes probed with Ham-D13 antibody.

Different Western Blots are shown in FIG. 1 to show PrP$^C$ expression in mammalian muscle tissue. Specifically, FIG. 1A is an image of a Western blot depicting the level of PrP$^C$ expression in various tissues of an FVB mouse. The highest level of PrP$^C$ is in brain (Br), but distinct bands corresponding to fully glycosylated PrP$^C$ are also seen in lanes with skeletal muscle (Sk Mu) and heart (He) homogenates. Very faint bands apparently representing partially glycosylated PrP$^C$ are found in lanes bearing liver (Li) and kidney (Ki) homogenates. No bands are seen in tissues from an FVB/Prnp$^{0/0}$ mouse. The blot was probed with R073 serum. (b) Western blot comparing PrP$^C$ expression level in the brain and muscle of Bos taurus. Serial dilutions of brain homogenate from a single animal are compared to dilutions of muscle homogenates from two animals obtained from a different source. The amount of PrP$^C$ found in 25 µg of muscle homogenate is slightly greater than that seen in 1.3 µg brain homogenate, therefore PrP$^C$ expression in muscle is ~5 to 10% of that in brain. The PrP$^C$ derived from muscle in this blot migrates faster than that derived from brain because the muscle is from animals bearing a 5-octarepeat PRNP allele, while brain is derived from an animal with the 6-octarepeat allele (Goldmann, et al., "Different forms of the bovine PrP gene have five or six copies of a short, G-C-rich element within the protein-coding exon," *J. Gen. Virol.*, 72:201–204 (1991)).

Figure 4:
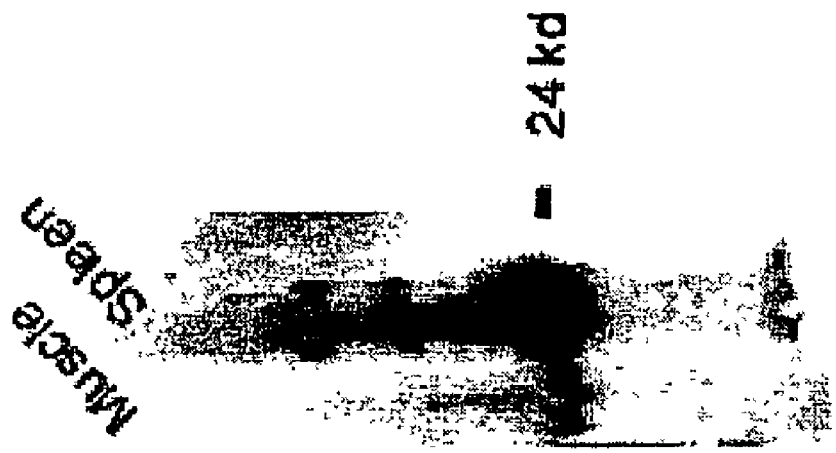
FIG. 4 shows images of muscle and spleen tissues extracted from a human who died of pathogenically confirmed CJD.

The results shown have determined that PrP$^C$ is expressed in human muscle and that PrP$^{Sc}$ accumulated in the muscle of a patient with CJD (See FIG. 4). When 50 mg of quadriceps was prepared as described in the Methods disclosed and described here, a ~27kD band was found by Western blotting using an anti-PrP Fab'.

FIG. 4 shows that PrP$^{Sc}$ accumulates in the muscle of humans with CJD. Quadriceps muscle and spleen were obtained from a patient who had died of pathologically confirmed CJD. Homogenates were digested with proteinase K as described in the Methods, and the equivalent of 50 mg tissue loaded in each lane. The blot was probed with Hum-P, a recombinant Fab' recognizing human PrP. The approximately 25kD band seen in muscle and spleen represents the protease resistant core of PrP$^{Sc}$.

These results all indicate that PrP$^{Sc}$ will be found in bovine muscle from cattle with BSE. The results provided here indicate that a failure of the RIII mouse bioassay to detect prions in the skeletal muscle of cattle with BSE (Wells, et al., "Preliminary observations on the pathogenesis of experimental bovine spongiform encephalopathy (BSE): an update," *Vet. Rec.*, 142:103–106 (1998)) should be re-examined using the highly sensitive bioassays in Tg(BoPrP) Prnp$^{0/0}$ (Scott, et al., "Identification of a prion protein epitope modulating transmission of bovine spongiform encephalopathy prions to transgenic mice," *Proc. Natl. Acad. Sci. USA*, 94:14279–14284 (1999); Scott, et al., "Compelling transgenetic evidence for transmission of bovine spongiform encephalopathy prions to humans," *Proc. Natl. Acad. Sci. USA*, 96:15137–15142 (1999)). Sensitive immunoassays may also be useful in determining PrP$^{Sc}$ levels in muscle from cattle or cervids with prion disease (Safar, et al., "Eight prion strains have PrP$^{Sc}$ molecules with different conformations," *Nat. Med.*, 4:1157–1165 (1998)). Results provided here showing that muscle in mice both propagates and accumulates prions makes the accurate determination of prion titers in bovine muscles more urgent than previously assumed.

Methods

Transgene Constructs

MCK-SHaPrP. A 3.3 kbp fragment of the promoter/enhancer region of the mouse muscle creatine kinase (MCK) gene directs chloramphenicol acetyl transferase (CAT) expression to skeletal muscle and myocardium (Johnson, et al., "Muscle creatine kinase sequence elements regulating skeletal and cardiac muscle expression in transgenic mice." *Mol. Cell. Biol.*, 9:3393–3399 (1989)). The beta-galactosidase coding sequence in pNASS-beta (Clonetech) was replaced with the coding sequence for full-length SHaPrP and ligated the MCK promoter/enhancer into the Xho 1 site of the vector. In the completed construct, SV40 splice donor and acceptor sites are situated between the MCK promoter and the Syrian hamster open reading frame (ORF). This "artificial intron" may increase expression of the transgene (Choi, et al., "A generic intron increases gene expression in transgenic mice," *Mol. Cell Biol.*, 11:3070–3074 (1991)).

α-actin-MoPrP. A fragment of the chicken α-actin gene, extending from position −191 to position +27 relative to the transcriptional start site, directs expression of a CAT gene to skeletal muscle (Petropoulos, et al., "The chicken skeletal muscle alpha-actin promoter is tissue specific in transgenic mice," *Mol. Cell. Biol.*, 9:3785–3792 (1989)). This 218 bp fragment was ligated to a derivative of the mouse PrP gene in which the promoter/enhancer elements and the 12-kbp second intron had been deleted (Fischer, et al., "Prion protein (PrP) with amino-proximal deletions restoring susceptibility of PrP knockout mice to scrapie," *EMBO J.*, 15:1255–1264 (1996)).

TTR-MoPrP. An approximately 300 bp sequence containing the promoter and an enhancer sequence from the mouse transthyretin (TTR) gene was linked to the same modified fragment of the mouse PrP gene used in the α-actin-MoPrP construct described above. The transthyretin promoter/enhancer sequence used had been previously demonstrated to direct expression to the liver and brain, with occasional expression in the kidney (Costa, et al., "The cell-specific enhancer of the mouse transthyretin (prealbumin) gene binds a common factor at one site and a liver-specific factor(s) at two other sites," *Mol. Cell. Biol.*, 8:81–90 (1988)).

Microinjections and Screening

The transgene constructs were introduced into FVB/Prnp$^{0/0}$ mice. Incorporation of the α-actin-MoPrP and TTR-MoPrP transgenes was detected by hybridization of tail DNA with a murine PrP-specific probe, while the presence of the MCK-SHaPrP transgene was determined by polymerase chain reaction on tail DNA using primers which amplify across the MCK-SHaPrP junction.

Analysis of PrP Expression

Organ homogenates were prepared in phosphate buffered saline (PBS). For skeletal muscle, the proximal hind limb muscles were homogenized. After determining the protein concentration by the bicinchonic acid (BCA) assay (Pierce), indicated amounts of total protein were analyzed by Western blotting according to standard procedures (Sambrook, et al., "Molecular Cloning—A Laboratory Manual, 2nd Ed. (Cold Spring Harbor Laboratory Press, Cold Spring Harbor, N.Y.) (1989)) using a chemiluminescent detection system (ECL, Amersham). Blots were probed with R073, a polyclonal rabbit antiserum that recognizes mouse and hamster PrP (Serban, et al., "Rapid detection of Creutzfeldt-Jakob disease and scrapie prion proteins," *Neurology*, 40:110–117 (1990)); Hum-D13, a recombinant antibody recognizing mouse PrP (Peretz, et al., "Strain-specified relative conformational stability of the scrapie prion protein," *Protein Sci.*, 10:854–863 (2001)); 3F4, a monoclonal antibody that recognizes hamster but not mouse PrP (Kascsak, et al., "Mouse polyclonal and monoclonal antibody to scrapie-associated fibril proteins," *J. Virol.*, 61:3688–3693 (1987)); or HumP, a recombinant antibody that recognizes bovine PrP (J. Safar, personal communication). PrP expression levels were determined by visual inspection of serial dilutions of the appropriate homogenates on Western blots.

Detection of PrP$^{Sc}$ in Skeletal Muscle

Mouse muscle homogenates were pulverized under liquid nitrogen, suspended to 10% in PBS then subjected to 10 strokes of a Potter-Elvehjem homogenizer. For proteinase digestion, an equal volume of 4% Sarkosyl in PBS was added to 1 to 4 ml of the homogenate and PK was added at a ratio of 1:50, PK to homogenate total protein. The sample was incubated at 37° C. for 1 h with rocking, then a proteinase inhibitor cocktail (Complete, Boehringer-Mannheim) was added. Phosphotungstic acid (PTA) precipitation was performed as described (Safar, et al., "Eight prion strains have PrP$^{Sc}$ molecules with different conformations," *Nat. Med.*, 4:1157–1165 (1998)), except that samples were subjected to centrifugation at 20,000 ×g at 4° C. in a fixed angle rotor. Western blotting and detection were performed as described above. Relative amounts of brain and muscle PrP$^{Sc}$ were determined by comparing densities of bands obtained from serial dilutions of brain homogenate to bands representing muscle-derived PrP$^{Sc}$ on Western blots. NIH Image software analysis of flatbed scanner digitized images of photographic film was used to quantify band densities and interpolate PrP$^{Sc}$ amounts in muscle relative to those in brain. Mean values obtained from analyses of several exposures of differing durations are reported. Human muscle was prepared as was mouse muscle except that homogenization was done using a disposable plastic tissue grinder, and the PTA precipitation was omitted.

Inoculation of Mice with Prions

I.m.- or i.p-inoculated mice received 50 µl (approximately $10^7$ D$_{50}$ units of prions) of a 10% pooled brain homogenate either from Syrian hamsters inoculated with Sc237 prions or from CD-1 mice inoculated with RML prions showing signs of scrapie. I.c.-inoculated Tg(TTR-MoPrP)8332/Prnp$^{0/0}$ mice received 30 µl of a final 1% homogenate of RML-infected mouse brain (approximately $10^5$ ID$_{50}$ units).

Incubation Time Assays

Prion titers in organ homogenates were determined by an incubation time assay. Tissue from Tg(MCK-SHaPrP)8775/Prnp$^{0/0}$ mice, which express hamster PrP, were assayed in Syrian hamsters (Prusiner, et al., "Measurement of the scrapie agent using an incubation time interval assay," *Ann. Neurol.*, 11:353–358 (1982); Prusiner, et al., *Prion Biology and Diseases* (ed. Prusiner, S. B.) 653–715 (Cold Spring Harbor Laboratory Press, Cold Spring Harbor, N.Y.) (1999)). Tissues from Tg(α-actin-MoPrP)6906/Prnp$^{0/0}$ and Tg(TTR-MoPrP) 8332/Prnp$^{0/0}$ mice, which express mouse PrP, were assayed in Tg(MoPrP)4053/FVB mice, a transgenic line that overexpresses mouse Prnp$^a$ (Telling, et al., "Interactions between wild-type and mutant prion proteins modulate neurodegeneration in transgenic mice," *Genes & Dev.*, 10:1736–1750 (1996)). The incubation time-prion titer relationship for Tg(MoPrP)4053/FVB using the RML prion strain is: log titer ($ID_{50}$ units/g)=1+32.189* $e^{(-0.278*(mean\ inc.\ time\ (days)))}$ (Supattapone, et al., "Branched polyamines cure prion-infected neuroblastoma cells," *J. Virol.*, 75:3453–3461 (2001)). Incubation time assays are less accurate at estimating low prion titers than high titers. The convention applied here was to estimate that titers be less than $10^3$ $ID_{50}$ units/g if some, but not all, inoculated animals fall ill, and that titers be less than $10^2$ ID50 units/g if no animals fall ill. An alternative estimate of low titers can be obtained by assuming that since $(0.5^t)^N$ is the chance that no inoculated animals develop scrapie (where N is the number of animals inoculated and t is $ID_{50}$ unit titer per inoculum), the maximum titer that has at least a 5% chance of zero transmissions is 0.43 units/inoculum, or about $10^{3.2}$ $ID_{50}$ units/g tissue, which is therefore the lower limit of the sensitivity of the assay.

In some bioassays of Sc237 prions, all i.c.-inoculated hamsters developed disease, but prion titers calculated from equations describing standard curves of mean incubation time versus the titer resulted in estimated values significantly lower than 1 $ID_{50}$ unit per inoculation. In these cases, prion titers were reported as calculated to allow comparison with other experiments. Actual titers were likely to be significantly higher, since if all animals developed disease, the titer should be greater than the minimum necessary to result in at least a 5% chance that all inoculated animals would fall ill. This value is 1.7 $ID_{50}$ units/inoculum, or about $10^{3.5}$ $ID_{50}$ units/g tissue, when 8 animals are inoculated with 50 μl of a 1% homogenate, since the likelihood of all animals developing scrapie is $(1-0.5^t)^N$.

EXAMPLES

Distinctive Levels of PrP$^{Sc}$ Found in Particular Muscles

Materials and Methods

Detection of PrP$^{Sc}$ in Skeletal Muscle

Muscle tissue was pulverized under liquid nitrogen, suspended to 10% in phosphate buffered saline (PBS) then subjected to 10 strokes of a Potter-Elvehjem homogenizer. For protease digestion, an equal volume of 4% Sarkosyl in PBS was added to 1 to 4 ml of the homogenate and proteinase K (PK) was added at a ratio of 1:50, PK to homogenate protein. The sample was incubated at 37° C. for 1 h with rocking, followed by the addition of a proteinase inhibitor cocktail (Complete, Boehringer-Mannheim). Phosphotungstic acid precipitation was performed as described (Safar, J., Wille, H., Itri, V., Groth, D., Serban, H., Torchia, M., Cohen, F. E. & Prusiner, S. B. (1998) *Nat. Med.* 4, 1157–1165), except that samples were subjected to centrifugation at 20,000 ×g at 4° C. in a fixed angle rotor.

Western blotting and PrP detection were performed as described previously (Supattapone, S., Wille, H., Uyechi, L., Safar, J., Tremblay, P., Szoka, F. C., Cohen, F. E., Prusiner, S. B. & Scott, M. R. (2001) *J. Virol.* 75, 3453–3461). Relative amounts of brain and muscle $PrP^{Sc}$ were determined by comparing densities of bands obtained from serial dilutions of brain homogenate to bands representing muscle-derived $PrP^{Sc}$ on Western blots. NIH Image software analysis of digitized images of photographic film was used to quantify band densities and interpolate $PrP^{Sc}$ amounts in muscle relative to those in brain. Mean values obtained from analyses of several exposures of differing durations are reported.

For $PrP^{Sc}$ detection using ELISA, PK-digested muscle homogenates were denatured with 6 M guanidine thiocyanate after centrifugation described above. Subsequently denatured homogenates were immobilized on the surface of a 96-well Immulon II ELISA plate (Dynex) and the rest of the surface was blocked by 3% bovine serum albumin. Detection of $PrP^{Sc}$ was carried out by a 2 h incubation of HuM-D18 antibody (Peretz, D., Scott, M., Groth, D., Williamson, A., Burton, D., Cohen, F. E. & Prusiner, S. B. (2001) Protein Sci. 10, 854–863) in 1× Tris buffered saline, followed by 1 h incubation with goat anti-human Fab antibody conjugated to alkaline phophatase (Pierce). An additional 1 h incubation utilized 1-step pNPP (Pierce), an alkaline phosphatase substrate for the development of a colored product, which can be measured at 405 nm.

Inoculation of Mice with Prions

Mice were inoculated intramuscularly (i.m.) or intraperitoneally (i.p.) with 50 μl of a 10% pooled brain homogenate either from Syrian hamsters inoculated with Sc237 prions or from CD-1 mice inoculated with Rocky Mountain Laboratory (RML) prions showing signs of scrapie. The inoculum contained ~$10^7$ $ID_{50}$ units of prions. Mice inoculated intracerebrally (i.c.) received 30 μl of a final 1% homogenate of RML- or Me7-infected mouse brain (~$10^6$ $ID_{50}$ units).

Determination of Prion Titers

Prion titers in organ homogenates were determined by an incubation time assay. Tissue from Tg(MCK-SHaPrP)8775/$Prnp^{0/0}$ mice, which express Syrian hamster (SHa) PrP, were assayed in Syrian hamsters (Prusiner, S. B., Cochran, S. P., Groth, D. F., Downey, D. E., Bowman, K. A. & Martinez, H. M. (1982) *Ann. Neurol.* 11, 353–358; Prusiner, S. B., Kaneko, K., Cohen, F. E., Safar, J. & Riesner, D. (1999) in *Prion Biology and Diseases*, ed. Prusiner, S. B. (Cold Spring Harbor Laboratory Press, Cold Spring Harbor), pp. 653–715). Tissues from Tg(α-actin-MoPrP)6906/$Prnp^{0/0}$ and Tg(TTR-MoPrP)8332/$Prnp^{0/0}$ mice, which express mouse (Mo) PrP, were assayed in Tg(MoPrP)4053/FVB mice, a transgenic line that overexpresses mouse $Prnp^a$ (Telling, G. C., Haga, T., Torchia, M., Tremblay, P., DeArmond, S. J. & Prusiner, S. B. (1996) *Genes& Dev.* 10, 1736–1750). The relationship between incubation time and prion titer for Tg(MoPrP)4053/FVB using the RML prion strain is: log titer ($ID_{50}$ units/g)=1+32.189* $e^{(-0.0278*(mean\ inc.\ time\ (days))}$ (Supattapone, S., Wille, H., Uyechi, L., Safar, J., Tremblay, P., Szoka, F. C., Cohen, F. E., Prusiner, S. B. & Scott, M. R. (2001) *J. Virol.* 75, 3453–3461). Incubation time assays are less accurate at estimating low prion titers than high titers. The convention applied in this paper was to estimate titers to be less than $10^3$ $ID_{50}$ units/g if some, but not all, inoculated animals became ill, and titers to be less than $10^2$ $ID_{50}$ units/g if no animals became ill. An alternative estimate of low titers can be obtained by assuming that since $(0.5^t)^N$ is the chance that no inoculated animals develop disease (in which N is the number of animals inoculated and t is $ID_{50}$ unit titer per inoculum), the maximum titer that has at least a 5% chance of zero transmissions is 0.43 units/inoculum, or about $10^{3.2}$ ID50 units/g tissue, which is therefore the lower limit of the sensitivity of the assay. In some bioassays of Sc237 prions, all i.c. inoculated hamsters developed disease, but prion titers calculated from equations describing standard curves of mean incubation time versus the titer resulted in estimated values significantly lower than 1 $ID_{50}$ unit per inoculation. In these cases, prion titers were reported as calculated to allow comparison with other experiments. Actual titers were likely to be significantly higher, because if all animals developed disease, the titer should be greater than the minimum necessary to result in at least a 5% chance that all inoculated animals would become ill. This value is 1.7 $ID_{50}$ units/inoculum, or about $10^{3.5}$ $ID_{50}$ units/g tissue, when eight animals are inoculated with 50 μl of a 1% homogenate, because the likelihood of all animals developing disease is $(1-0.5^t)^N$.

Transgene Constructs

MCK-SHaPrP. A 3.3 kbp fragment of the promoter/enhancer region of the mouse muscle creatine kinase (MCK) gene directs chloramphenicol acetyl transferase (CAT) expression to skeletal muscle and myocardium (Johnson, J. E., Wold, B. J. & Hauschka, S. D. (1989) *Mol. Cell. Biol.* 9, 3393–3399). We replaced the beta-galactosidase coding sequence in pNASS-beta (Clonetech) with the coding sequence for full-length SHaPrP and ligated the MCK promoter/enhancer into the Xho1 site of the vector. In the completed construct, SV40 splice donor and acceptor sites are situated between the MCK promoter and the Syrian hamster open reading frame. This "artificial intron" may increase expression of the transgene (Choi, T., Huang, M., Gorman, C. & Jaenisch, R. (1991) *Mol. Cell. Biol.* 11, 3070–3074).

α-actin-MoPrP. A fragment of the chicken α-actin gene, extending from position −191 to position +27 relative to the transcriptional start site, directs expression of a CAT gene to skeletal muscle (Petropoulos, C. J., Rosenberg, M. P., Jenkins, N. A., Copeland, N. G. & Hughes, S. H. (1989) *Mol Cell. Biol.* 9, 3785–3792). We ligated this 218 bp fragment to a derivative of the mouse PrP gene in which the promoter/enhancer elements and the 12-kbp second intron had been deleted (Fischer, M., Rüilicke, T., Raeber, A., Sailer, A., Moser, M., Oesch, B., Brandner, S., Aguzzi, A. & Weissmann, C. (1996) *EMBO J.* 15, 1255–1264).

TTR-MoPrP. An approximately 300 bp sequence containing the promoter and an enhancer sequence from the mouse transthyretin (TTR) gene was linked to the same modified fragment of the mouse PrP gene used in the α-actin-MoPrP construct described above. The TTR promoter/enhancer sequence used had been previously demonstrated to direct expression to the liver and brain, with occasional expression in the kidney (Costa, R. H., Lai, E., Grayson, D. R. & Darnell, J. E., Jr. (1988) *Mol. Cell. Biol.* 8, 81–90).

Microinjections and Screening

The transgene constructs were introduced into FVB/Prnp$^{0/0}$ mice. Incorporation of the α-actin-MoPrP and TTR-MoPrP transgenes was detected by hybridization of tail DNA with a murine PrP-specific probe while the presence of the MCK-SHaPrP transgene was determined by polymerase chain reaction on tail DNA using primers, which amplify across the MCK-SHaPrP junction.

Analysis of PrP Expression

Organ homogenates were prepared in PBS. For skeletal muscle, we homogenized the proximal hindlimb muscles. After determining the protein concentration by the bicinchonic acid (BCA) assay (Pierce), indicated amounts of total protein were analyzed by Western blotting according to standard procedures (Sambrook, J., Fritsch, E. F. & Maniatis, T. (1989) *Molecular Cloning—A Laboratory Manual, 2nd Ed.* (Cold Spring Harbor Laboratory Press, Cold Spring Harbor, N.Y.)) using a chemiluminescent detection system (ECL, Amersham). Blots were probed with R073, a polyclonal rabbit antiserum that recognizes mouse and hamster PrP (Serban, D., Taraboulos, A., DeArmond, S. J. & Prusiner, S. B. (1990) *Neurology* 40, 110–117); HuM-D13, a recombinant antibody recognizing mouse PrP (Peretz, D., Scott, M., Groth, D., Williamson, A., Burton, D., Cohen, F. E. & Prusiner, S. B. (2001) *Protein Sci.* 10, 854–863); 3F4, a monoclonal antibody that recognizes hamster but not mouse PrP (Kascsak, R. J., Rubenstein, R., Merz, P. A., Tonna-DeMasi, M., Fersko, R., Carp, R. I., Wisniewski, H. M. & Diringer, H. (1987) *J. Virol.* 61, 3688–3693); or HuM-P, a recombinant antibody that recognizes bovine PrP (J. Safar, personal communication). We determined PrP expression levels by visual inspection of serial dilutions of the appropriate homogenates on Western blots.

Results

Substantial Prion Titers in Muscle

Because PrP$^C$ expression is essential for prion propagation, we first used Western blot analysis to confirm that in both mice and cattle (*Bos taurus*) PrP$^C$ is expressed in skeletal muscle, at a level about 5 to 10% of that in brain (FIG. 5; Horiuchi, M., Yamazaki, N., Ikeda, T., Ishiguro, N. & Shinagawa, M. (1995) *J. Gen. Virol.* 76, 2583–2587; Bendheim, P. E., Brown, H. R., Rudelli, R. D., Scala, L. J., Goller, N. L., Wen, G. Y., Kascsak, R. J., Cashman, N. R. & Bolton, D. C. (1992) *Neurology* 42, 149–156). We then used an incubation time assay to determine that prion titers in the hindlimb muscle of FVB mice showing signs of disease. Muscle harvested from mice sacrificed 128 days after i.c. inoculation with RML prions harbored titers of $10^5$ to $10^6$ ID50 units/g (Table 4).

TABLE 4

Prion titers in tissues of wt FVB mice*

| Tissue assayed | Animal no. | Mean incubation time [days ± SEM (n/n₀)†] | Log titer ID$_{50}$ units/g‡ ± SEM |
|---|---|---|---|
| Muscle | G70155 | 66 ± 1.7 (10/10) | 6.1 ± 0.2 |
| | G70158 | 70 ± 2.4 (10/10) | 5.6 ± 0.3 |
| | G70155 | 64 ± 2.5 (10/10) | 6.4 ± 0.3 |
| | G70157 | 73 ± 2.1 (10/10) | 5.2 ± 0.3 |
| Liver | G70155 | 103 (2/10) | <3 |
| | G70157 | — (0/10) | <2 |

*Mice were sacrificed when showing signs of neurologic illness, 128 days after intracerebral inoculation with RML prions.
†n, number of animals diagnosed ill with scrapie; n₀, number of animals inoculated.
‡Determined by incubation time assay in Tg(MoPrP)4053/FVB mice.

These surprisingly high titers of prions in muscle do not represent a general contamination of mouse organs with brain-derived prions because homogenates of liver, an organ that in wild-type (wt) mice expresses almost no PrP$^C$ (Raeber, A. J., Sailer, A., Hegyi, I., Klein, M. A., Rulike, T., Fischer, M., Brandner, S., Aguzzi, A. & Weissmann, C. (1999) *Proc. Natl. Acad. Sci. USA* 96, 3987–3992), from these same mice either failed to transmit scrapie or transmitted to only a few mice, indicating titers of $10^3$ ID$_{50}$ units/g or less. Previous studies demonstrated that brain prion titers in mice exhibiting signs of prion infection are typically $10^9$ to $10^{10}$ ID50 units/g (Supattapone, S., Wille, H., Uyechi, L., Safar, J., Tremblay, P., Szoka, F. C., Cohen, F. E., Prusiner, S. B. & Scott, M. R. (2001) *J. Virol.* 75, 3453–3461) when assayed in Tg(MoPrP)4053/FVB mice.

Figure 5A:
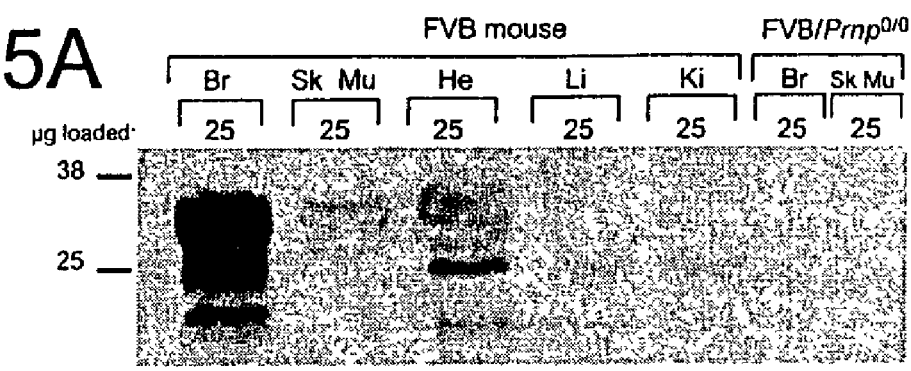
FIG. 5 includes Western Blots showing levels of $PrP^C$ expression in mammalian muscle with 5a showing the highest expression in brain and 5b showing no expression in 0/0 PrP knock-out mice.
Figure 5B:
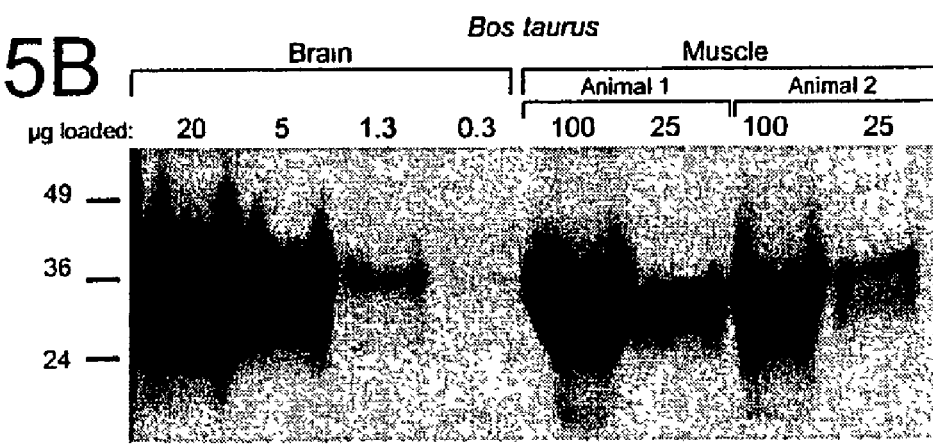

FIG. 5(a) is a Western blot depicting the level of $PrP^C$ expression in various tissues of an FVB mouse. The highest level of $PrP^C$ is in brain (Br), but distinct bands corresponding to fully glycosylated $PrP^C$ are also seen in lanes with skeletal muscle (Sk Mu) and heart (He) homogenates. Faint bands apparently representing partially glycosylated $PrP^C$ are found in lanes bearing liver (Li) and kidney (Ki) homogenates. No bands are seen in tissues from an FVB/Prnp$^{0/0}$ mouse. The blot was probed with the R073 polyclonal antiserum. FIG. 5(b) shows Western blots comparing $PrP^C$ expression level in the brain and muscle of *Bos taurus*. Serial dilutions of brain homogenate from a single animal were compared to dilutions of muscle homogenates from two animals obtained from a different source. The amount of $PrP^C$ found in 25 μg of muscle homogenate is slightly greater than that seen in 1.3 μg brain homogenate. These results show that $PrP^C$ expression in muscle is ~5 to 10% of that in brain. The $PrP^C$ derived from muscle in this blot migrated faster than that derived from brain because the muscle is from cattle bearing a 5-octarepeat PRNP allele, whereas brain is derived from an animal with the 6-octarepeat allele (Goldmann, W., Hunter, N., Martin, T., Dawson, M. & Hope, J. (1991) *J. Gen. Virol.* 72, 201–204).

$PrP^{Sc}$ Differentially Accumulates in Specific Muscle Groups

To confirm the high titers of infectious prions we found in skeletal muscle, we used Western immunoblots to detect the presence of protease-resistant $PrP^{Sc}$. We initially examined the hindlimb muscle of wt CD-1 mice showing signs of neurologic disease 128 days after i.c. inoculation with RML prions (FIG. 6a). Muscle homogenates from these mice, but not from uninoculated controls, displayed PK-resistant $PrP^{Sc}$ of an apparent molecular weight and glycoform ratio identical to that of $PrP^{Sc}$ found in the brain. Comparison of muscle and serial dilutions of brain homogenates on Western blots demonstrated that protease-resistant $PrP^{Sc}$ in muscle was ~500-fold lower than in the brain (data not shown). This brain/muscle $PrP^{Sc}$ ratio of $10^{2.7}$ is similar to the brain/muscle prion titer ratio of approximately $10^3$.

We next examined the distribution of $PrP^{Sc}$ in various muscle groups. For these studies, we used mice showing signs of disease at 138 or 146 days after i.c. inoculation with the Me7 strain of murine prions. Again, we observed substantial PK-resistant $PrP^{Sc}$ accumulation in the hindlimb muscle (FIG. 6b). In contrast, we did not detect $PrP^{Sc}$ accumulation in the skeletal muscle from other regions, including head and neck, back or forelimb, with an exception of the forelimb muscle from a single mouse (FIG. 6c). To confirm the region-specific $PrP^{Sc}$ accumulation shown in the Western blot analysis, we measured the levels of $PrP^{Sc}$ using ELISA, which gives more quantitative results than Western blotting (Table 5). Only muscle from the hindlimbs of infected mice, and the forelimb muscle of the one mouse described above, had values significantly above background.

FIG. 6(a) shows five lanes wherein Lane 1 contains untreated brain homogenate from an uninoculated CD-1 mouse. All other lanes contain insoluble fractions from PK-digested homogenates of CD-1 mouse muscle. No protease-resistant $PrP^{Sc}$ was found in the muscle of uninoculated mice (lane 2) whereas $PrP^{Sc}$ was readily detectable in the muscle of mice showing signs of neurologic disease 132 days after intracerebral inoculation with RML prions (lanes 4 and 5). For comparison, brain homogenate from a mouse showing signs of disease was diluted 1:1000 into a muscle homogenate from an uninoculated mouse (lane 3). Amounts loaded are expressed as equivalents of total protein (in mg) of homogenate, before proteinase digestion and precipitation. Note that lanes 4 and 5 were loaded with the product of twice as much original homogenate as lanes 2 and 3.

In FIG. 6(b) hindlimb skeletal muscles of three ill FVB mice inoculated with Me7 prions were homogenized and subjected to analysis. These mice showed typical clinical signs of scrapie at 138 days (MK70665) and 146 days (MK70658, MK70659) after intracerebral inoculation with Me7 prions. Samples were digested with PK (lanes 2, 4, 6) or undigested (lanes 1, 3, 5). Two mg of PK-digested muscle homogenates and about 60 μg of undigested muscle homogenates were used for analysis.

In FIG. 6(c) muscle tissue from the head-neck (HN), back (B) and forelimb (FL) of the mice analyzed in panel b were collected at the time that the hindlimb muscle was collected. Lanes were loaded with PK-digested (even numbered lanes) and undigested muscle homogenates (odd numbered lanes). The analytical method was same as that described in panel b. All blots were probed with the HuM-D13 antibody.

TABLE 5

Differential protease-resistant $PrP^{Sc}$ accumulation in various regions of muscle tissue from mice inoculated i.c. with Me7 prions.

| | $OD_{405}$ Mean ± S.D.* | | | |
|---|---|---|---|---|
| Animal ID | head/neck | back | forelimb | hindlimb |
| Uninoculated control 1 | 0.038 ± 0.015 | 0.091 ± 0.017 | 0.038 ± 0.008 | 0.036 ± 0.007 |
| Uninoculated control 2 | 0.057 ± 0.002 | 0.040 ± 0.006 | 0.059 ± 0.006 | 0.049 ± 0.001 |
| MK70658 | 0.032 ± 0.005 | 0.026 | 0.110 ± 0.063 | 0.414 ± 0.006 |
| MK70659 | 0.043 ± 0.004 | 0.095 | 0.124 | 0.492 ± 0.023 |
| MK70665 | 0.047 ± 0.001 | 0.055 ± 0.011 | 0.498 ± 0.059 | 0.499 ± 0.029 |
| P value† | 0.38 | 0.63 | 0.02 | <0.000001 |

*Mean and standard deviation (S.D) were obtained from duplicates or triplicates of ELISA. Numbers without S.D. were obtained from single ELISA determinations.
†P values were calculated comparing all muscle of uninoculated mice to muscle of the indicated region from all inoculated mice, using the t-test with an alpha of 0.0125 to correct for multiple comparisons.

Intrinsic Prion Replication in Muscle

Muscle tissue is composed of a variety of cell types (Engel, A. & Banker, B. Q. (1986) *Myology*: basic and clinical (McGraw-Hill, New York)), and is intimately associated with neural tissue. To determine if prions replicate in myofibers, we constructed two lines of transgenic (Tg) mice that express PrP only under the control of myocyte-specific promoters. For each line, we introduced transgenes into FVB mice in which the chromosomal PrP gene had been disrupted (Prnp$^{0/0}$) (Telling, G. C., Haga, T., Torchia, M., Tremblay, P., DeArmond, S. J. & Prusiner, S. B. (1996) *Genes & Dev.* 10, 1736–1750; Büeler, H., Fisher, M., Lang, Y., Bluethmann, H., Lipp, H.-P., DeArmond, S. J., Prusiner, S. B., Aguet, M. & Weissmann, C. (1992) *Nature* 356, 577–582). In the first line, designated Tg($\alpha$-actin-MoPrP) 6906/Prnp$^{0/0}$, the chicken $\alpha$-actin promoter directs expression of the mouse Prnp$^a$ allele. In the second line, designated Tg(MCK-SHaPrP)8775/Prnp$^{0/0}$, the MCK promoter drives the expression of SHaPrP.

Skeletal muscle from Tg($\alpha$-actin-MoPrP)6906/Prnp$^{0/0}$ mice (FIG. 7a) expresses PrP$^C$ at a level that is about 8-fold higher than the level found in the brains of wt mice. Low levels of PrP$^C$ are produced in cardiac muscle and PrP$^C$ is barely detectable in brain. In the Tg(MCK-SHaPrP)8775/Prnp$^{0/0}$ line, the level of PrP$^C$ expression in muscle is 4-fold higher than the level of PrP$^C$ that is expressed in hamster brain. Tg(MCK-SHaPrP)8775/Prnp$^{0/0}$ mice express low levels of PrP$^C$ in cardiac muscle, and no PrP$^C$ was detected in the brain (FIG. 7b).

We inoculated the Tg mice and non-Tg littermates i.m. in the left hindlimb with prions and then sacrificed the mice at various times after inoculation. Tg(MCK-SHaPrP)8775/Prnp$^{0/0}$ mice were inoculated with hamster Sc237 prions. We inoculated Tg($\alpha$-actin-MoPrP)6906/Prnp$^{0/0}$ mice with RML prions and in parallel, inoculated FVB/Prnp$^{0/0}$ mice, which are incapable of propagating prions (Büeler, H., Aguzzi, A., Sailer, A., Greiner, R.-A., Autenried, P., Aguet, M. & Weissmann, C. (1993) *Cell* 73, 1339–1347; Prusiner, S. B., Groth, D., Serban, A., Koehler, R., Foster, D., Torchia, M., Burton, D., Yang, S.-L. & DeArmond, S. J. (1993) *Proc. Natl. Acad. Sci. USA* 90, 10608–10612), with the same prion strain. We used incubation time assays to determine prion titers in homogenates of muscle from the hindlimb contralateral to the inoculated one, the brain and the spleen.

Figure 7A:
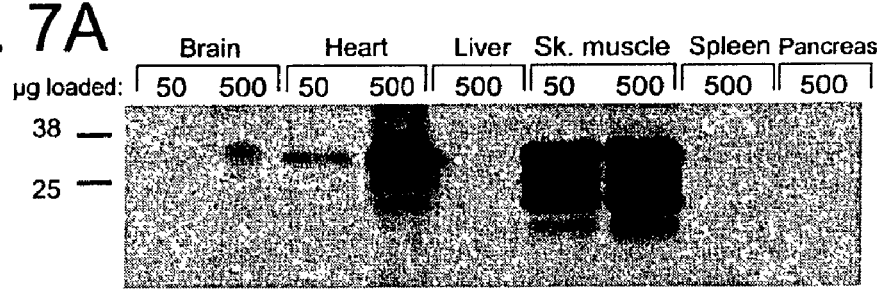
FIG. 7 includes Western Blots of different types of tissue where 7(a) shows higher expression in muscle; 7(b) shows only expression in muscle; 7(c) shows expression almost exclusively in muscle.
Figure 7B:
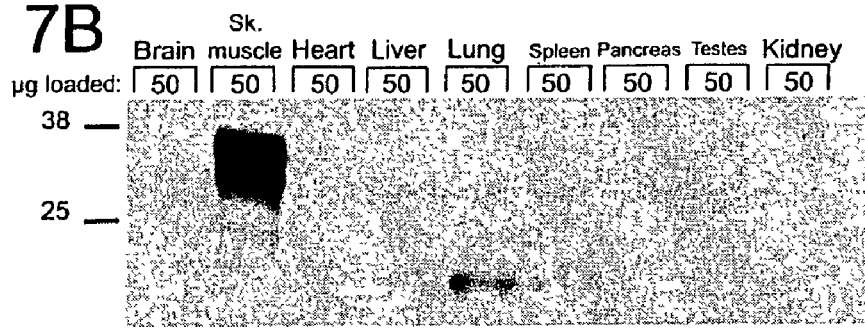
Figure 7C:
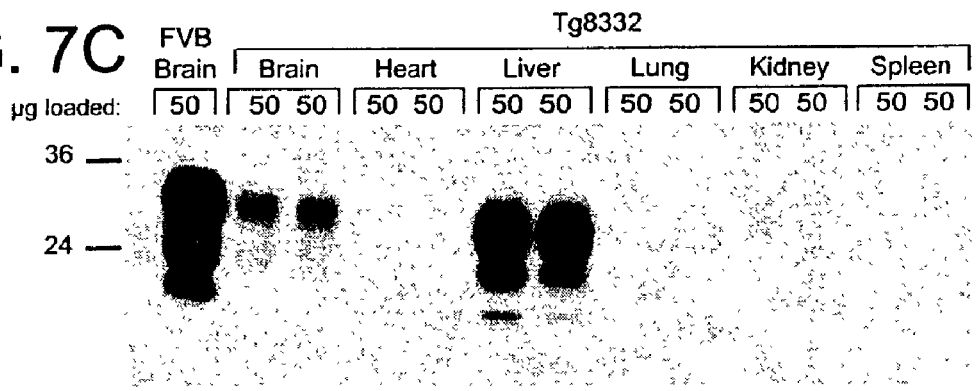

FIG. 7 shows Western blots depicting the distribution of PrP$^C$ in transgenic mice. Specifically, in FIG. 7(a) Tg($\alpha$-actin-MoPrP)6906/Prnp$^{0/0}$ mouse probed with the polyclonal antibody R073. PrP$^C$ expression in muscle is about 8-fold higher than in wt mouse brain (not shown). (b) Tg(MCK-SHaPrP)8775/Prnp$^{0/0}$ mouse probed with 3F4, a monoclonal antibody that recognizes hamster PrP$^C$. PrP$^C$ expression is only detectable in skeletal muscle (Sk. Muscle). A longer exposure of this blot (not shown) revealed trace expression in cardiac muscle, but no PrP$^C$ was detected in any other organ. The low molecular weight bands, seen most prominently in lane 5 (Lung), were also seen when the anti-mouse Ig secondary antibody was used without prior incubation with 3F4. (c) Homogenates of organs from two Tg(TTR-MoPrP) FVB/Prnp$^{0/0}$ mice compared to FVB brain. Blot was probed with R073. PrP$^C$ expression in liver is lower than in FVB brain, but higher than in the brain of mice of this transgenic line. A very small amount of PrP$^C$ is expressed in the kidney. Glycosylated forms of PrP$^C$ from the liver migrate slightly faster than the corresponding glycoforms from the brain of these same mice or of FVB mice.

From Tg($\alpha$-actin-MoPrP)6906/Prnp$^{0/0}$ mice inoculated with RML prions, we found titers of >$10^7$ ID$_{50}$ units/g in muscle, obtained at 350 days after inoculation. Titers were generally lower in muscles of Tg(MCK-SHaPrP)8775/Prnp$^{0/0}$ mice inoculated with Sc237 prions, at ~$10^4$ ID$_{50}$ units/g in two mice and $10^8$ ID$_{50}$ units/g in another mouse, all three of which were sacrificed 413 days after inoculation (Table 6). The muscle prion titer in a fourth mouse sacrificed 76 days after inoculation was ~$10^4$ ID$_{50}$ units/g. We did not detect prions in muscle homogenates from uninoculated Tg($\alpha$-actin-MoPrP)6906/Prnp$^{0/0}$ and Tg(MCK-SHaPrP) 8775/Prnp$^{0/0}$ mice.

Several experiments were conducted to confirm that the prions found in muscle were formed therein. Results from two experiments exclude residual inoculum as the source of the prions measured. First, no prions were detected in the muscle of the FVB/Prnp$^{0/0}$ mice, which are incapable of propagating prions (Büeler, H., Aguzzi, A., Sailer, A., Greiner, R.-A., Autenried, P., Aguet, M. & Weissmann, C. (1993) *Cell* 73, 1339–1347; Prusiner, S. B., Groth, D., Serban, A., Koehler, R., Foster, D., Torchia, M., Burton, D., Yang, S.-L. & DeArmond, S. J. (1993) *Proc. Natl. Acad. Sci. USA* 90, 10608–10612), at 350 days after i.m. inoculation with RML prions, indicating that the prions had been cleared. Second, because it is conceivable that FVB/Prnp$^{0/0}$ mice clear prions more efficiently than mice expressing PrP$^C$ (Race, R. & Chesebro, B. (1998) *Nature* 392, 770), we inoculated both Tg(MCK-SHaPrP)8775/Prnp$^{0/0}$ and FVB/Prnp$^{0/0}$ mice with Sc237 prions, then determined prion titers in the inoculated muscle at various intervals (Table 7). Prions disappeared equally rapidly from both lines. Moreover, the levels of prions found ipsilateral to the injection site at 28 days after inoculation in Tg(MCK-SHaPrP)8775/Prnp$^{0/0}$ mice were at least 10-fold lower than the levels found contralateral to the injection site in mice sacrificed at later times, indicating de novo prion synthesis (compare Tables 6 and 7).

TABLE 6

Prion titers in tissues of transgenic mice

| Line | Inoculum (route) | Interval* | Tissue assayed | Animal no. | Mean incubation time [days ± SEM (n/n$_0$)$^\dagger$] | Log titer ID$_{50}$ units/g‡ ± SEM |
|---|---|---|---|---|---|---|
| Tg(MCK-SHaPrP)8775/Prnp$^{0/0}$ | Sc237(i.m) | 413 | muscle** | E4041 | 82 ± 1.3 (8/8) | 7.4 ± 0.1 |
| | | 413 | | E4516 | 112 ± 0.7 (8/8) | 4.2 ± 0.1 |
| | | 413 | | E4509 | 114 ± 6.2 (8/8) | 4.0 ± 0.4 |
| | | 76 | | E4515 | 113 ± 2.4 (8/8) | 4.2 ± 0.1 |
| | | 413 | Brain | E4509 | — (0/8) | <2 |
| | | 76 | Spleen | E4515 | 211 (5/8) | <3 |
| | | 413 | | E4516 | 220 (3/8) | <3 |
| | none | N.A. | Muscle | D16745 | — (0/8) | <2 |
| | | | | D16746 | — (0/8) | <2 |

TABLE 6-continued

Prion titers in tissues of transgenic mice

| Line | Inoculum (route) | Interval* | Tissue assayed | Animal no. | Mean incubation time [days ± SEM (n/n₀)†] | Log titer ID$_{50}$ units/g‡ ± SEM |
|---|---|---|---|---|---|---|
| Tg(α-actin-MoPrP)6906/Prnp$^{0/0}$ | RML(i.m.) | 350 | Muscle | E9812 | 58 ± 2 (10/10) | 7.4 ± 0.4 |
| | | 350 | | E9813 | 59 ± 2 (10/10) | 7.2 ± 0.4 |
| | | 350 | Brain | E9812 | 105 (2/10) | <3 |
| | | 350 | | E9813 | 126 (4/10) | <3 |
| | | 350 | Spleen | E9812 | 424 (3/5) | <3 |
| | | 350 | | E9813 | 201 (6/7) | <3 |
| FVB/Prnp$^{0/0}$ | RML (i.m.) | 350 | Muscle | E8979 | — (0/10) | <2 |
| | | 350 | | E8980 | — (0/10) | <2 |
| Tg(TTR-MoPrP)8332/Prnp$^{0/0}$ | RML (i.p.) | 523 | Liver | E10176 | 197 (3/10) | <3 |
| | | 523 | | E10177 | 93 ± 3.2 (10/10) | 3.4 ± 0.2 |
| | RML (i.c.) | 296 | Liver | MF4691 | 91 ± 2.9 (10/10) | 3.8 ± 0.2 |
| | | 296 | | MF4692 | 97 (7/8) | <3 |
| | | 296 | Brain | MF4691 | 51 ± 2.5 (10/10) | 8.8 ± 0.6 |
| | | 296 | | MF4692 | 55 ± 2.1 (10/10) | 8.0 ± 0.5 |
| | None | N.A. | Liver | ME9012 | — (0/10) | <2 |

*Number of days from inoculation to sacrifice of animal.
†n, number of animals diagnosed ill with scrapie; n₀, number of animals inoculated.
‡Tg(MCK-SHaPrP)8775/Prnp$^{0/0}$ tissue prion titers determined by incubation time assay in Syrian hamsters. All others assayed in Tg(MoPrP)4053/FVB mice.
**Muscle tissue is from the hindlimb contralateral to the hindlimb that was injected with the prion inoculum.

TABLE 7

Decline of prion titers in muscle agter inoculation With Sc237 Prions.

| Line | Interval between inoculation and harvest | Mean incubation time [days ± SEM (n/n₀)†] | Log titer* (ID$_{50}$ units/g ± SEM) |
|---|---|---|---|
| Tg(MCK-SHaPrP)8775/PrnP$^{0/0}$ | 4 hours | 112.5 ± 3.3 (8/8) | 3.9 ± 0.3 |
| | | 90 ± 4.3 (8/8) | 6.8 ± 0.5 |
| | 1 day | 85.8 ± 2.0 (8/8) | 6.2 ± 0.2 |
| | | 92.5 ± 1.3 (8/8) | 5.3 ± 0.2 |
| | 7 days | 118 ± 2.3 (8/8) | 3.0 ± 0.1 |
| | | 114.4 ± 4.9 (8/8) | 4.8 ± 0.4 |
| | 28 days | 184.5 ± 4.6 (8/8) | −0.6 ± 0.3 |
| | | — (0/8) | — |
| FVB/Prnp$^{0/0}$ | 4 hours | 87.4 ± 1.0 (8/8) | 6.0 ± 0.1 |
| | | 115.8 ± 1.3 (8/8) | 3.0 ± 0.1 |
| | 1 day | 109.6 ± 2.7 (8/8) | 3.5 ± 0.2 |
| | | 101.9 ± 1.5 (8/8) | 4.2 ± 0.2 |
| | 7 days | 114 ± 3.0 (8/8)) | 3.2 ± 0.2 |
| | | 182.1 ± 8.1 (8/8) | 0.5 ± 0.5 |
| | 28 days | 174.3 ± 5.7 (8/8) | 0.4 ± 0.4 |
| | | 200.3 ± 9.7 (4/8) | — |

†n, number of animals diagnosed ill with scrapie; n₀, number of animals inoculated.
*Determined by incubation time assay in i.c.-inoculated hamsters. In some cases, very long incubation periods result in low calculated titers, which are likely to be underestimations (see Methods). These values are reported for purposes of comparison.

In order to exclude the possibility that the prions found in the muscle were contaminants produced elsewhere in our mice, we determined prion titers in the brains and spleens of Tg mice inoculated i.m. No prions were detected in Tg(MCK-SHaPrP)8775/Prnp$^{0/0}$ mouse brain, but low titers were found in Tg(α-actin-MoPrP)6906/Prnp$^{0/0}$ brain, a finding consistent with the low level of PrP$^C$ produced there. We also found low prion titers in the spleens of inoculated mice from both lines, which might represent an accumulation of prions formed elsewhere, since Western blot analysis failed to detect splenic PrP$^C$ in these lines. The titers in spleen and brain were, in all cases, lower than in muscle; therefore, the titers in muscle were unlikely to be due to contamination from other tissues.

Tg(α-actin-MoPrP)6906/Prnp$^{0/0}$ and Tg(MCK-SHaPrP) 8775/Prnp$^{0/0}$ mice spontaneously developed a myopathy, in accordance with findings in mice, in which PrP$^C$ is overexpressed under control of the SHaPrP promoter (Westaway, D., DeArmond, S. J., Cayetano-Canlas, J., Groth, D., Foster, D., Yang, S.-L., Torchia, M., Carlson, G. A. & Prusiner, S.

B. (1994) *Cell* 76, 117–129). We detected similar histologic abnormalities in the muscle of prion-inoculated mice and uninoculated Tg controls.

Hepatocytes Ineffeciently Accumulate Prions

To determine whether prions can propagate in hepatocytes, we used Tg(TTR-MoPrP)8332/Prnp$^{0/0}$ mice, in which a fragment of the TTR promoter directs mouse Prnp$^a$ expression simultaneously to the liver and to a subset of brain neurons (FIG. 7c), with higher PrP levels in liver than in brain. We inoculated the mice i.c. with RML prions and sacrificed them when they developed signs of disease, at 296 days. To test the influence of inoculation site, we also inoculated Tg(TTR-MoPrP)8332/Prnp$^{0/0}$ mice i.p. with RML prions.

Prion titers in the brains of Tg(TTR-MoPrP)8332/Prnp$^{0/0}$ mice inoculated i.c. with RML prions were $10^8$–$10^9$ ID$_{50}$ units/g whereas hepatic prion titers were only ~$10^3$ ID$_{50}$ units/g. Tg(TTR-MoPrP)8332/Prnp$^{0/0}$ mice inoculated i.p. with RML prions never appeared ill and were sacrificed 523 days after inoculation. Hepatic prion titers in the mice inoculated i.p. were similar to those of mice inoculated i.c. Although hepatic prion titers were low, it does appear that expressing high levels of PrP$^C$ in liver enhances prion formation, since liver homogenates from Tg(TTR-MoPrP)8332/Prnp$^{0/0}$ mice inoculated with RML prions transmitted disease to significantly more mice than did liver homogenates from RML-inoculated FVB mice (Tables 4 and 6, P<0.001, Fisher exact test).

These data show that different cells types accumulate prions with markedly different efficiencies, even when PrP$^C$ expression levels are similar. Comparing three tissues in Tg mice expressing murine PrP$^C$, RML prion titers were ~$10^9$ ID$_{50}$ units/g in brain, ~$10^3$ ID$_{50}$ units/g in liver (for Tg(TTR-MoPrP)8332/Prnp$^{0/0}$ mice)) and $10^7$ ID$_{50}$ units/g in hindlimb skeletal muscle (for Tg(α-actin-MoPrP)6906/Prnp$^{0/0}$ mice). The differing levels of prion accumulation may be due in part to the restricted expression of auxiliary proteins that have been postulated to participate in prion replication (Kaneko, K., Zulianello, L., Scott, M., Cooper, C. M., Wallace, A. C., James, T. L., Cohen, F. E. & Prusiner, S. B. (1997) *Proc. Natl. Acad. Sci. USA* 94, 10069–10074; Zulianello, L., Kaneko, K., Scott, M., Erpel, S., Han, D., Cohen, F. E. & Prusiner, S. B. (2000) *J. Virol.* 74, 4351–4360). The apparently different glycosylation of hepatic PrP$^C$ may contribute to the inefficient prion accumulation seen there, but brain and muscle PrP$^{Sc}$ displayed different levels of accumulation despite indistinguishable glycoforms. Notable is a study by other investigators (Raeber, A. J., Sailer, A., Hegyi, I., Klein, M. A., Rulike, T., Fischer, M., Brandner, S., Aguzzi, A. & Weissmann, C. (1999) *Proc. Natl. Acad. Sci. USA* 96, 3987–3992) who concluded that prions failed to propagate in hepatocytes or T-cells of Tg mice that express PrP in these cell types. However, the authors stated that the levels of PrP expression achieved in the livers of their mice were quite low and that the absence of detectable prions in circulating T-cells might have been due to loss of prion-infected cells during natural turnover or because of prion-related toxicity.

DISCUSSION

The above experiments demonstrate that mouse skeletal muscle is intrinsically capable of propagating prions, that titers at least as high as $10^7$ ID$_{50}$ units/g can accumulate in muscle, and most surprisingly, that the efficiency of this accumulation varies markedly among groups of muscles taken from different regions of the body. Our finding of prion accumulation in skeletal muscle seems unambiguous, in that we obtained similar results with two different prion strains in wt mice and in transgenic mice expressing PrP$^C$ almost exclusively in skeletal muscle. Why prions accumulate more efficiently in certain muscles than in others is not clear. However, different skeletal muscle groups demonstrate differential susceptibility to a number of diseases processes, a property that presumably reflects biochemical differences in skeletal muscles of different body regions.

Studies in transgenic mice (Telling, G. C., Scott, M., Mastrianni, J., Gabizon, R., Torchia, M., Cohen, F. E., DeArmond, S. J. & Prusiner, S. B. (1995) *Cell* 83, 79–90) and cultured cells (Kaneko, K., Zulianello, L., Scott, M., Cooper, C. M., Wallace, A. C., James, T. L., Cohen, F. E. & Prusiner, S. B. (1997) *Proc. Natl. Acad. Sci. USA* 94, 10069–10074; Zulianello, L., Kaneko, K., Scott, M., Erpel, S., Han, D., Cohen, F. E. & Prusiner, S. B. (2000) *J. Virol.* 74, 4351–4360) have implicated a cellular factor other than PrP, provisionally termed prion protein modulator factor "PPMF", that is needed for the efficient propagation of prions. Perhaps only some skeletal muscles have sufficient amounts of PPMF to enable the accumulation of high titers of prions. Similarly, the inefficient accumulation of prions in hepatic tissue demonstrated by our studies is further evidence of a role for an auxiliary factor such as PPMF in prion propagation.

That high prion titers may be found in skeletal muscle even if CNS and lymphatic tissues are carefully excluded from the muscle raises the concern that humans consuming meat from prion-infected animals are at risk for acquiring infection. However, several caveats must be considered when assessing the risk of humans developing disease from prion-tainted meat. First, the efficiency of prion accumulation in muscle may vary with either the host species or the prion strain involved. Indeed, mouse RML prions appear to have accumulated more efficiently in muscle than did hamster Sc237 prions. Second, oral transmission is inefficient compared to the i.c. inoculations used for the bioassays reported in this study. In hamsters, oral exposure is $10^5$- to $10^9$-fold less efficient that the i.c. route (Prusiner, S. B., Cochran, S. P. & Alpers, M. P. (1985) *J. Infect. Dis.* 152, 971–978; Diringer, H., Roehmel, J. & Beekes, M. (1998) *J. Gen. Virol.* 79, 609–612). Finally, the species barrier must be considered. In many cases, efficient transmission of prions from one species to another requires a high degree of homology in the amino-acid sequence of PrP between the two species. However, the degree to which amino-acid sequence influences the efficiency of transmission depends upon the strain of prion. In the case of nvCJD prions, Tg mice expressing bovine PrP$^C$ are much more susceptible to nvCJD prions, derived from human brain, than are Tg mice expressing either human or chimeric human-mouse PrP$^C$ (Scott, M. R., Will, R., Ironside, J., Nguyen, H.-O. B., Tremblay, P., DeArmond, S. J. & Prusiner, S. B. (1999) *Proc. Natl. Acad. Sci. USA* 96, 15137–15142; Hill, A. F., Desbruslais, M., Joiner, S., Sidle, K. C. L., Gowland, I., Collinge, J., Doey, L. J. & Lantos, P. (1997) *Nature* 389, 448–450).

Previous studies have generally reported low prion titers in muscle tissue. Some of these studies used inefficient cross-species transmissions, which might be responsible for their failure to detect prions in muscle (Wells, G. A. H., Hawkins, S. A. C., Green, R. B., Austin, A. R., Dexter, I., Spencer, Y. I., Chaplin, M. J., Stack, M. J. & Dawson, M. (1998) *Vet. Rec.* 142, 103–106). Our investigations reveal another potential explanation for this failure. Since muscle prion accumulation varies between muscle groups, or perhaps between specific muscles, previous studies may have failed to sample the muscles bearing the highest prion titers. If prions accumulate in certain muscles of humans with prion disease to levels near those that we found in mice with prion disease, it should be possible to definitively diagnose all forms of CJD and related disorders using muscle tissue for biopsy. This approach would offer significant advantages over the relatively difficult and morbid brain biopsy procedure, which is currently the only way to definitively diagnose prion disease in humans.

The above results indicate that prions accumulate in skeletal muscle of cattle with BSE, of sheep with scrapie, or of deer and elk with CWD remains to be established. However, our findings indicate that a comprehensive and systematic effort to determine the distribution of prions in the skeletal muscle of animals with prion disease is urgently needed. The distribution of prions in muscle may vary with the animal species, perhaps even with breeds, varieties and lines within a species as well as with the strain of prions. Such assays need to be carried out using sensitive and quantitative techniques, such bioassays in transgenic mice and quantitative immunoassays adapted to $PrP^{Sc}$ detection in muscle tissue.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of preparing a sample, comprising the steps of:
    obtaining a sample of muscle tissue from a mammal;
    homogenizing the sample thereby creating a homogenate;
    contacting the homogenate with a complexing agent which binds $PrP^{Sc}$ in the homogenate forming a complex with a higher specific gravity as compared to the specific gravity of either $PrP^{Sc}$ or the complexing agent alone; and
    concentrating the complex by the application of gravity.

2. The method of claim 1, wherein the muscle tissue is from muscle having a higher concentration of prions than other muscle for the species of mammal from which the sample is obtained.

3. The method of claim 2, wherein the sample is obtained from muscle having a higher concentration of prions as compared to any other muscle in the mammal from which the muscle is obtained.

4. The method of claim 1, wherein the sample of muscle tissue is obtained from hind limb muscle of the mammal chosen from a cow, a sheep and a deer wherein the concentration by gravity is enhanced by centrifugation.

5. The method of claim 1, wherein the complexing agent is chosen from a heteropoly acid and a salt thereof.

6. The method of claim 5, wherein the complexing agent is sodium phosphotungstate.

7. The method of claim 1, further comprising:
    treating the homogenate under conditions and for a period of time so as to denature $PrP^{C}$ in the homogenate and so as to change the conformation of $PrP^{Sc}$ in the homogenate.

* * * * *

UNITED STATES PATENT AND TRADEMARK OFFICE
CERTIFICATE OF CORRECTION

PATENT NO.          : 7,166,477 B2
APPLICATION NO. : 10/211942
DATED                    : January 23, 2007
INVENTOR(S)          : Stanley B. Prusiner et al.

It is certified that error appears in the above-identified patent and that said Letters Patent is hereby corrected as shown below:

In column 32, lines 4-33, please make the amendments as shown:

1.    A method of preparing a sample, comprising the steps of:

obtaining a sample of muscle tissue <u>obtained</u> from <u>hind limb muscle of a mammal selected from the group consisting of a cow, a sheep and a deer</u>;

homogenizing the sample thereby creating a homogenate;

contacting the homogenate with a complexing agent which binds $PrP^{Sc}$ in the homogenate forming a complex <u>comprising the complexing agent and the $PrP^{Sc}$</u> with a higher specific gravity as compared to the specific gravity of ~~either~~ $PrP^{Sc}$ ~~or the complexing agent~~ alone; and concentrating the complex by the application of gravity.

2.    The method of claim 1, wherein the muscle tissue is from muscle having a higher concentration of prions than other muscle for the species of mammal from which the sample is obtained.

3.    The method of claim 2, wherein the sample is obtained from muscle having a higher concentration of prions as compared to any other muscle in the mammal from which the muscle is obtained.

4.    The method of claim 1 , wherein ~~the sample of muscle tissue is obtained from hind limb muscle of the mammal chosen from a cow, a sheep and a deer wherein~~ the concentration by gravity is enhanced by <u>centrifugation</u> ~~contriguation~~.

5.    The method of claim 1, wherein the complexing agent is ~~chosen from~~ <u>selected from the group consisting of</u> a heteropoly acid and a salt thereof.

6.    (Original) The method of claim 5, wherein the complexing agent is sodium phosphotungstate.

UNITED STATES PATENT AND TRADEMARK OFFICE
CERTIFICATE OF CORRECTION

PATENT NO. : 7,166,477 B2
APPLICATION NO. : 10/211942
DATED : January 23, 2007
INVENTOR(S) : Stanley B. Prusiner et al.

It is certified that error appears in the above-identified patent and that said Letters Patent is hereby corrected as shown below:

7.    (Currently Amended) The method of claim 1, further comprising:

treating the homogenate <u>with a denaturant</u> under conditions and for a period of time so as to denature $PrP^C$ in the homogenate and so as to change the conformation of $PrP^{Sc}$ in the homogenate <u>in a manner so that an epitope is exposed on the denatured $PrP^{Sc}$ in the changed conformation which epitope was not exposed prior to treating the $PrP^{Sc}$</u>.

Signed and Sealed this

Eleventh Day of September, 2007

JON W. DUDAS
*Director of the United States Patent and Trademark Office*